(12) United States Patent
Gotsch

(10) Patent No.: US 10,699,373 B1
(45) Date of Patent: Jun. 30, 2020

(54) LIGHT FIELD DISPLAY, ADJUSTED PIXEL RENDERING METHOD THEREFOR, AND VISION CORRECTION SYSTEM AND METHOD USING SAME

(71) Applicant: EVOLUTION OPTIKS LIMITED, Bridgetown (BB)

(72) Inventor: Daniel Gotsch, Redwood City, CA (US)

(73) Assignee: EVOLUTION OPTIKS LIMITED, Bridgetown (BB)

( * ) Notice: Subject to any disclaimer, the term of this patent is extended or adjusted under 35 U.S.C. 154(b) by 0 days.

(21) Appl. No.: 16/830,893

(22) Filed: Mar. 26, 2020

Related U.S. Application Data

(63) Continuation of application No. 16/551,572, filed on Aug. 26, 2019, now Pat. No. 10,636,116, which is a
(Continued)

(30) Foreign Application Priority Data

Oct. 22, 2018 (CA) ...................... 3021636

(51) Int. Cl.
*G06T 3/20* (2006.01)
*G06T 3/40* (2006.01)
(Continued)

(52) U.S. Cl.
CPC ............ *G06T 3/20* (2013.01); *G06K 9/00604* (2013.01); *G06T 3/40* (2013.01); *G06T 5/003* (2013.01); *G06T 7/70* (2017.01); *G06T 19/006* (2013.01)

(58) Field of Classification Search
CPC ............ G06T 2207/30041; G06T 3/20; G06T 19/006; G06T 5/003; G06T 3/40; G06T 7/70; G06K 9/00604
See application file for complete search history.

(56) References Cited

U.S. PATENT DOCUMENTS

| 5,959,664 A | 9/1999 | Woodgate |
| 6,192,341 B1 | 2/2001 | Becker et al. |
| (Continued) | | |

FOREIGN PATENT DOCUMENTS

| AU | 2015100739 A4 | 7/2015 |
| DE | 102004038822 A1 | 3/2006 |
| (Continued) | | |

OTHER PUBLICATIONS

"A Computational Light Field Display for Correcting Visual Aberrations," Huang, F.C., Technical Report No. UCB/EECS-2013-206, Electrical Engineering and Computer Sciences University of California at Berkeley, http://www.eecs.berkeley.edu/Pubs/TechRpts/2013/EECS-2013-206.html, Dec. 15, 2013.
(Continued)

*Primary Examiner* — Todd Buttram
(74) *Attorney, Agent, or Firm* — Knobbe, Martens, Olson & Bear, LLP

(57) ABSTRACT

Described are various embodiments of a computer-implemented method, automatically implemented by one or more digital processors, to automatically adjust user perception of an input image to be rendered on a digital display via a set of pixels thereof, wherein the digital display has an array of light field shaping elements (LFSE). In one embodiment, the method comprises: digitally mapping the input image on a retinal plane of the user, and for each pixel digitally projecting an adjusted image ray trace between said given pixel and a given LFSE to intersect said retinal plane at a given adjusted image location, given an estimated direction of a light field emanated by said given pixel given said given LFSE and a modeled redirection of said adjusted image ray trace in accordance with a designated eye focus parameter; associating an adjusted image value designated for said given adjusted image location with said given pixel based on
(Continued)

said mapping; rendering each said given pixel according to said adjusted image value associated therewith, thereby rendering a perceptively adjusted version of the input image.

24 Claims, 25 Drawing Sheets

Related U.S. Application Data continuation-in-part of application No. 16/259,845, filed on Jan. 28, 2019, now Pat. No. 10,394,322.

(51) Int. Cl.
| | | |
|---|---|---|
| *G06T 7/70* | (2017.01) | |
| *G06T 5/00* | (2006.01) | |
| *G06T 19/00* | (2011.01) | |
| *G06K 9/00* | (2006.01) | |

(56) References Cited

U.S. PATENT DOCUMENTS

| | | | |
|---|---|---|---|
| 6,386,707 B1 | 5/2002 | Pellicano | |
| 6,536,907 B1 | 3/2003 | Towner | |
| 6,543,898 B1 | 4/2003 | Griffin et al. | |
| 6,784,905 B2 | 8/2004 | Brown et al. | |
| 6,809,704 B2 | 10/2004 | Kulas | |
| 6,876,758 B1 | 4/2005 | Polat et al. | |
| 6,953,249 B1* | 10/2005 | Maguire, Jr. | H04N 5/74 345/7 |
| 7,062,547 B2 | 6/2006 | Brown et al. | |
| 7,517,086 B1 | 4/2009 | Kürkure | |
| 7,866,817 B2 | 1/2011 | Polat | |
| 7,891,813 B2 | 2/2011 | Ogilvie | |
| 7,973,850 B2 | 7/2011 | Ishiga | |
| 8,089,512 B2 | 1/2012 | Okabe et al. | |
| 8,098,440 B2 | 1/2012 | Jethmalani et al. | |
| 8,164,598 B2 | 4/2012 | Kimpe | |
| 8,231,220 B2 | 7/2012 | Baranton | |
| 8,322,857 B2 | 12/2012 | Barbur et al. | |
| 8,540,375 B2 | 9/2013 | Destain | |
| 8,717,254 B1 | 5/2014 | Nave et al. | |
| 8,783,871 B2 | 7/2014 | Pamplona et al. | |
| 8,798,317 B2 | 8/2014 | Wu | |
| 8,823,742 B2 | 9/2014 | Kweon | |
| 8,967,809 B2 | 3/2015 | Kirschen et al. | |
| 9,010,929 B2 | 4/2015 | Lewis | |
| 9,041,833 B2 | 5/2015 | Hatakeyama | |
| 9,052,502 B2 | 6/2015 | Caldeira et al. | |
| 9,066,683 B2 | 6/2015 | Zhou | |
| 9,104,233 B2 | 8/2015 | Alberth | |
| 9,159,299 B2 | 10/2015 | Lee | |
| 9,177,355 B1 | 11/2015 | Buchheit | |
| 9,183,806 B2 | 11/2015 | Felt | |
| 9,492,074 B1 | 11/2016 | Lee et al. | |
| 9,844,323 B2 | 12/2017 | Pamplona et al. | |
| 9,895,057 B2 | 2/2018 | Tumlinson | |
| 10,058,241 B2 | 8/2018 | Patella et al. | |
| 10,085,631 B2 | 10/2018 | Shimizu et al. | |
| 10,182,717 B2 | 1/2019 | Lindig et al. | |
| 10,206,566 B2 | 2/2019 | Skolianos et al. | |
| 10,247,941 B2 | 4/2019 | Fürsich | |
| 10,335,027 B2 | 7/2019 | Pamplona et al. | |
| 10,345,590 B2 | 7/2019 | Samec et al. | |
| 10,394,322 B1* | 8/2019 | Gotsch | G06F 1/1609 |
| 10,420,467 B2 | 9/2019 | Krall et al. | |
| 2006/0119705 A1 | 6/2006 | Liao | |
| 2008/0309764 A1 | 12/2008 | Kubota et al. | |
| 2009/0290132 A1 | 11/2009 | Shevlin | |
| 2011/0019056 A1 | 1/2011 | Hirsch et al. | |
| 2011/0122144 A1 | 5/2011 | Gabay | |
| 2011/0157180 A1 | 6/2011 | Burger et al. | |
| 2012/0113389 A1 | 5/2012 | Mukai et al. | |
| 2012/0206445 A1* | 8/2012 | Chiba | H04N 13/315 345/419 |
| 2012/0254779 A1 | 10/2012 | Ollivierre et al. | |
| 2012/0262477 A1 | 10/2012 | Buchheit | |
| 2013/0027384 A1 | 1/2013 | Ferris | |
| 2013/0096820 A1 | 4/2013 | Agnew | |
| 2013/0120390 A1 | 5/2013 | Marchand et al. | |
| 2013/0222652 A1 | 8/2013 | Akeley et al. | |
| 2014/0055692 A1 | 2/2014 | Kroll et al. | |
| 2014/0063332 A1 | 3/2014 | Miyawaki | |
| 2014/0118354 A1 | 5/2014 | Pais et al. | |
| 2014/0137054 A1 | 5/2014 | Gandhi et al. | |
| 2014/0200079 A1 | 7/2014 | Bathiche et al. | |
| 2014/0267284 A1 | 9/2014 | Blanche et al. | |
| 2014/0282285 A1 | 9/2014 | Sadhvani et al. | |
| 2014/0327750 A1 | 11/2014 | Malachowsky et al. | |
| 2014/0327771 A1 | 11/2014 | Malachowsky et al. | |
| 2015/0049390 A1 | 2/2015 | Lanman et al. | |
| 2015/0185501 A1 | 7/2015 | Bakaraju et al. | |
| 2015/0234187 A1 | 8/2015 | Lee | |
| 2015/0234188 A1 | 8/2015 | Lee | |
| 2015/0336511 A1 | 11/2015 | Ukeda | |
| 2016/0042501 A1 | 2/2016 | Huang et al. | |
| 2016/0103419 A1 | 4/2016 | Callagy et al. | |
| 2016/0134815 A1 | 5/2016 | Ishiguro et al. | |
| 2016/0306390 A1 | 10/2016 | Vertegaal et al. | |
| 2017/0027435 A1 | 2/2017 | Boutinon et al. | |
| 2017/0060399 A1 | 3/2017 | Hough et al. | |
| 2017/0227781 A1 | 8/2017 | Banerjee et al. | |
| 2017/0302913 A1 | 10/2017 | Tonar et al. | |
| 2017/0307898 A1 | 10/2017 | Vdovin et al. | |
| 2017/0353717 A1 | 12/2017 | Zhou et al. | |
| 2017/0365189 A1 | 12/2017 | Halpin | |
| 2018/0136486 A1 | 5/2018 | Macnamara et al. | |
| 2018/0252935 A1 | 9/2018 | Vertegaal et al. | |
| 2018/0290593 A1 | 10/2018 | Cho | |
| 2019/0125179 A1 | 5/2019 | Xu et al. | |
| 2019/0246095 A1* | 8/2019 | Kishimoto | G02C 13/00 |
| 2019/0246889 A1 | 8/2019 | Marin et al. | |

FOREIGN PATENT DOCUMENTS

| | | |
|---|---|---|
| EP | 2127949 A1 | 12/2009 |
| EP | 1509121 B1 | 9/2012 |
| FR | 3059537 B1 | 5/2019 |
| WO | 2011156721 A1 | 12/2011 |
| WO | 2013166570 A1 | 11/2013 |
| WO | 2014174168 A1 | 10/2014 |
| WO | 2014197338 A2 | 12/2014 |
| WO | 2018092989 A1 | 5/2018 |
| WO | 2018129310 A1 | 7/2018 |

OTHER PUBLICATIONS

"Eyeglasses-Free Display: Towards Correcting Visual Aberrations With Computational Light Field Displays," Huang, F.C. et al., ACM Transactions on Graphics (TOG)—Proceedings of ACM SIGGRAPH 2014, vol. 33, Issue 4, Article No. 59, Jul. 2014.

Agus M. et al., "GPU Accelerated Direct Volume Rendering on an interactive Light Field Display", EUROGRAPHICS 2008, vol. 27, No. 2, 2008

Burnett T., "FoVI3D Extreme Multi-view Rendering for Light-field Displays", GTC 2018 (GPU Technology Conference), Silicon Valley, 2018.

Halle M., "Autostereoscopic displays and computer graphics", Computer Graphics, ACM SIGGRAPH, 31(2), May 1997, pp. 58-62.

Masia B. et al., "A survey on computational displays: Pushing the boundaries of optics, computation, and perception", Computer & Graphics, vol. 37, 2013, pp. 1012-1038.

Wetzstein, G. et al., "Tensor Displays: Compressive Light Field Synthesis using Multilayer Displays with Directional Backlighting", https://web.media.mit.edu/~gordonw/TensorDisplays/TensorDisplays.pdf.

International Search Report for International Application No. PCT/CA2016/051006 dated Sep. 30, 2016 in 5 pages.

Written Opinion of the International Searching Authority received in International Application No. PCT/CA2016/051006 dated Sep. 30, 2016 in 9 pages.

(56) References Cited

OTHER PUBLICATIONS

Pamplona V. F. et al., "Tailored Displays to Compensate for Visual Aberrations," ACM Transactions on Graphics (TOG), Jul. 2012 Article No. 81, https://doi.org/10.1145/2185520.2185577.

Pamplona V. F., Thesis (Ph.D.)—Universidade Federal do Rio Grande do Sul. Programa de Pós-Graduação em Computação, Porto Alegre, BR—RS, 2012. Advisor: Manuel Menezes de Oliveira Neto.

"Eyeglasses-free Display: Towards Correcting Visual Aberrations with Computational Light Field Displays", by Huang et al., taken from http://web.media.mit.edu/~gordonw/VisionCorrectingDisplay/, publicshed Aug. 2, 2014, pp. 1-15.

Invitation to Pay Additional Fees and, Where Applicable, Protest Fee, issued on Feb. 7, 2020 for International Application No. PCT/IB2019/058955, 12 pages.

Andrew Maimone, et al. "Focus 3D: Compressive accommodation display," ACM Trans. Graph. 32.5 (2013).

Fattal, D. et al., A Multi-Directional Backlight for a Wide-Angle, Glasses-Free Three-Dimensional Display, Nature, Mar. 21, 2013, pp. 348-351, vol. 495.

\* cited by examiner

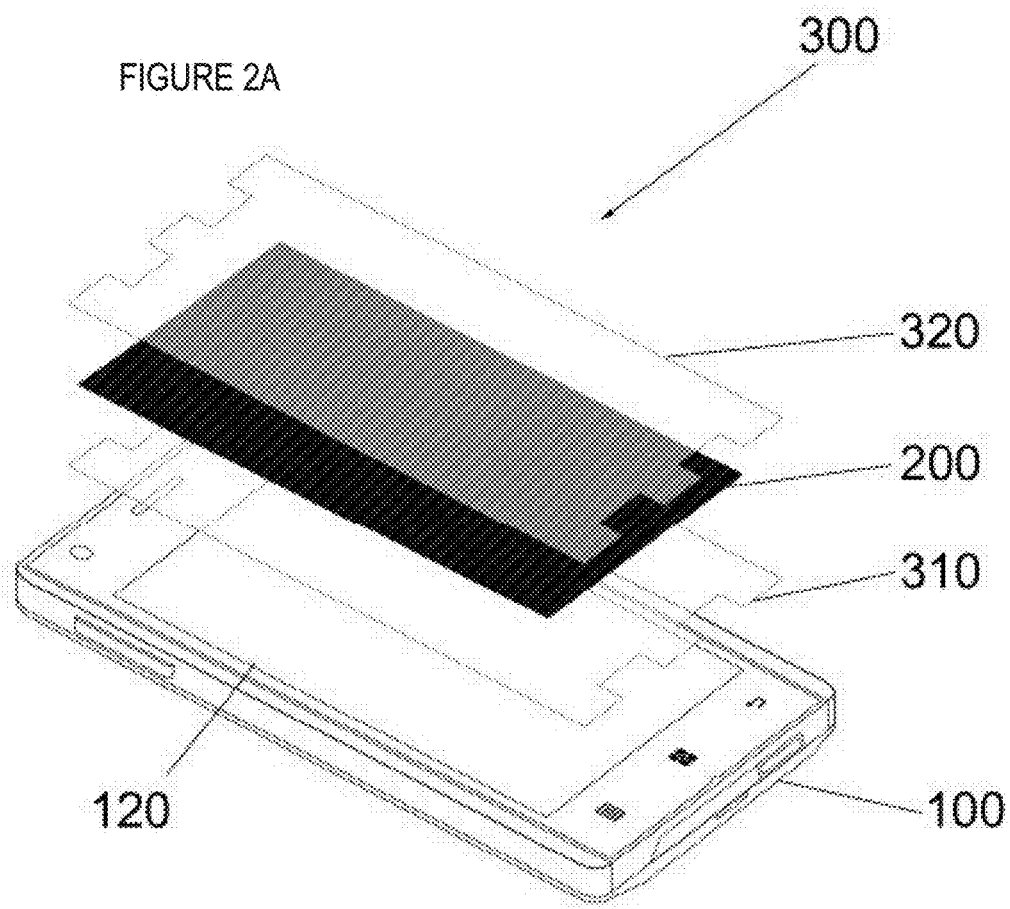
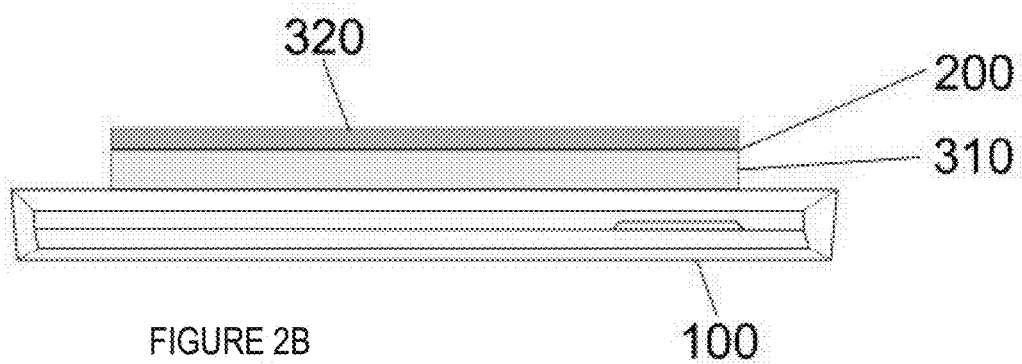

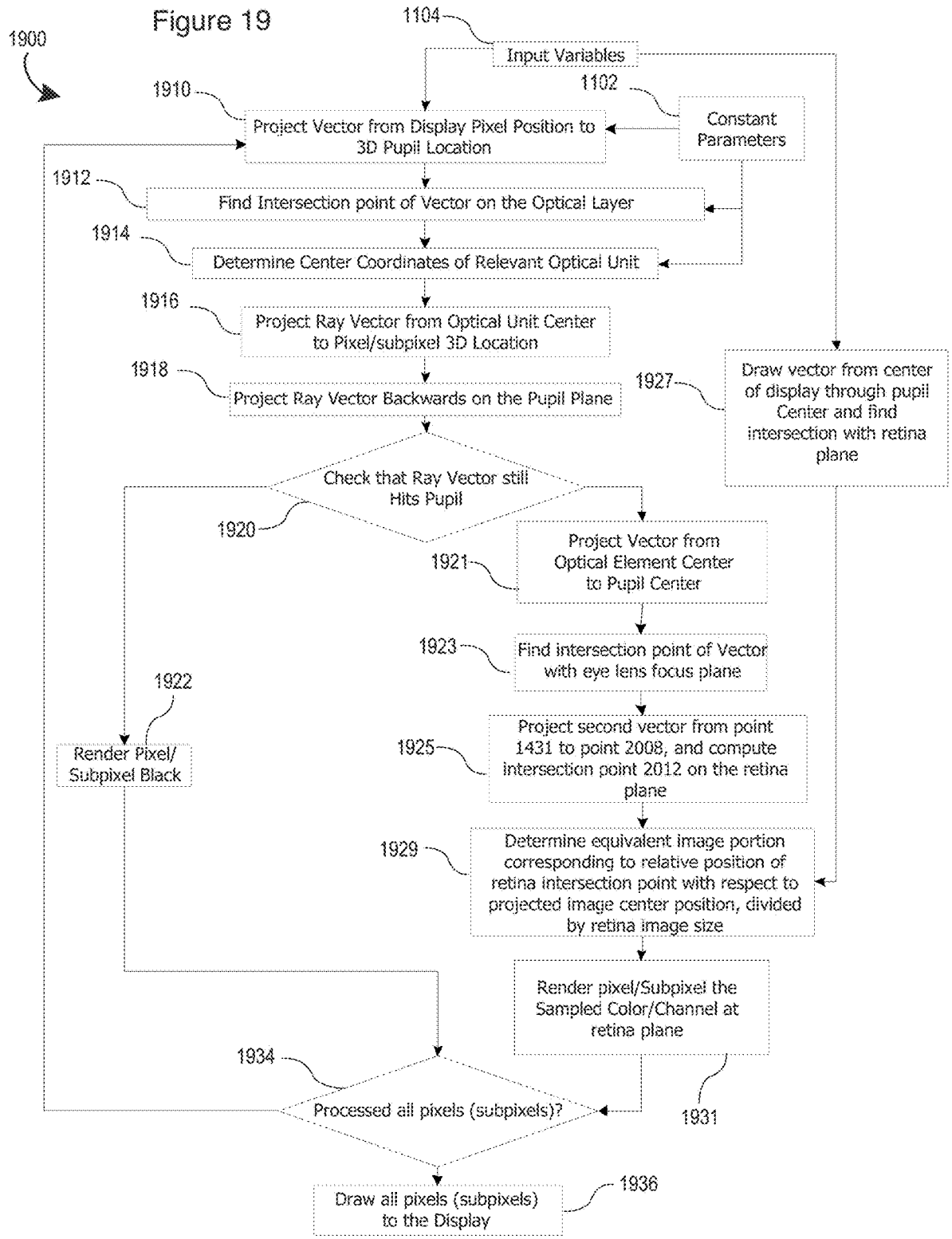

LIGHT FIELD DISPLAY, ADJUSTED PIXEL RENDERING METHOD THEREFOR, AND VISION CORRECTION SYSTEM AND METHOD USING SAME

CROSS REFERENCE TO RELATED APPLICATIONS

This application is a Continuation of U.S. patent application Ser. No. 16/551,572 filed Aug. 26, 2019, which is a Continuation-in-Part of U.S. patent application Ser. No. 16/259,845 filed Jan. 28, 2019, which claims priority to Canadian Patent Application No. 3,021,636 filed Oct. 22, 2018, the entire disclosure of each of which is hereby incorporated herein by reference.

FIELD OF THE DISCLOSURE

The present disclosure relates to digital displays, and in particular, to a light field display, and adjusted pixel rendering method and computer-readable medium therefor, and vision correction system and method using same.

BACKGROUND

Individuals routinely wear corrective lenses to accommodate for reduced vision acuity in consuming images and/or information rendered, for example, on digital displays provided, for example, in day-to-day electronic devices such as smartphones, smart watches, electronic readers, tablets, laptop computers and the like, but also provided as part of vehicular dashboard displays and entertainment systems, to name a few examples. The use of bifocals or progressive corrective lenses is also commonplace for individuals suffering from near and farsightedness.

The operating systems of current electronic devices having graphical displays offer certain "Accessibility" features built into the software of the device to attempt to provide users with reduced vision the ability to read and view content on the electronic device. Specifically, current accessibility options include the ability to invert images, increase the image size, adjust brightness and contrast settings, bold text, view the device display only in grey, and for those with legal blindness, the use of speech technology. These techniques focus on the limited ability of software to manipulate display images through conventional image manipulation, with limited success.

The use of 4D light field displays with lenslet arrays or parallax barriers to correct visual aberrations have since been proposed by Pamplona et al. (PAMPLONA, V., OLIVEIRA, M., ALIAGA, D., AND RASKAR, R.2012. "Tailored displays to compensate for visual aberrations." ACM Trans. Graph. (SIGGRAPH) 31.). Unfortunately, conventional light field displays as used by Pamplona et al. are subject to a spatio-angular resolution trade-off; that is, an increased angular resolution decreases the spatial resolution. Hence, the viewer sees a sharp image but at the expense of a significantly lower resolution than that of the screen. To mitigate this effect, Huang et al. (see, HUANG, F.-C., AND BARSKY, B. 2011. A framework for aberration compensated displays. Tech. Rep. UCB/EECS-2011-162, University of California, Berkeley, December; and HUANG, F.-C., LANMAN, D., BARSKY, B. A., AND RASKAR, R. 2012. Correcting for optical aberrations using multi layer displays. ACM Trans. Graph. (SiGGRAPH Asia) 31, 6, 185:1-185: 12) proposed the use of multilayer display designs together with prefiltering. The combination of prefiltering and these particular optical setups, however, significantly reduces the contrast of the resulting image.

Finally, in U.S. Patent Application Publication No. 2016/0042501 and Fu-Chung Huang, Gordon Wetzstein, Brian A. Barsky, and Ramesh Raskar. "Eyeglasses-free Display: Towards Correcting Visual Aberrations with Computational Light Field Displays". ACM Transaction on Graphics, xx:0, August 2014, the entire contents of each of which are hereby incorporated herein by reference, the combination of viewer-adaptive pre-filtering with off-the-shelf parallax barriers has been proposed to increase contrast and resolution, at the expense however, of computation time and power.

This background information is provided to reveal information believed by the applicant to be of possible relevance. No admission is necessarily intended, nor should be construed, that any of the preceding information constitutes prior art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for a light field display, adjusted pixel rendering method and computer-readable medium therefor, and vision correction system and method using same, that overcome some of the drawbacks of known techniques, or at least, provide a useful alternative thereto. Some aspects of disclosure provide embodiments of such systems, methods, displays and optical element arrays.

In accordance with one aspect, there is provided a computer-implemented method, automatically implemented by one or more digital processors, to automatically adjust user perception of an input image to be rendered on a digital display via a set of pixels thereof, wherein the digital display has an array of light field shaping elements (LFSE), the method comprising: digitally mapping the input image on a retinal plane of the user; for each given pixel of at least some of said pixels, digitally: projecting an adjusted image ray trace between said given pixel and a given LFSE to intersect said retinal plane at a given adjusted image location, given an estimated direction of a light field emanated by said given pixel given said given LFSE and a modeled redirection of said adjusted image ray trace in accordance with a designated eye focus parameter; associating an adjusted image value designated for said given adjusted image location with said given pixel based on said mapping; rendering each said given pixel according to said adjusted image value associated therewith, thereby rendering a perceptively adjusted version of the input image.

In one embodiment, the retinal plane is angled relative to the digital display. In one such embodiment, the retinal plane is modeled as a function of an input user pupil or eye location. In one such embodiment, the input user pupil or eye location is dynamically acquired via a digitally implemented pupil or eye tracker. In one such embodiment, the angle between said retinal plane and said digital display is dynamically updated based on data received from said pupil or eye tracker.

In one embodiment, the angle is dynamically updated based on acquired display inclination data.

In one embodiment, the mapping is implemented by scaling the input image on said retinal plane as a function of said designated eye focus parameter.

In one embodiment, the designated eye focus parameter is designated as a function of a quantified abnormal user eye focal length or a corrective eyewear prescription.

In one embodiment, the modeled redirection of said adjusted image ray trace is modelled in accordance with a non-linear eye focus parameter.

In one embodiment, the digital display is defined by a curved surface, and wherein said adjusted image ray trace is computed based on a vector normal to said curved surface for said pixel.

In accordance with another aspect, there is provided a non-transitory computer-readable medium comprising digital instructions to be implemented by one or more digital processors to automatically adjust user perception of an input image to be rendered on a digital display via a set of pixels thereof, wherein the digital display has an array of light field shaping elements (LFSE), by: digitally mapping the input image on a retinal plane of the user; for each given pixel of at least some of said pixels, digitally: projecting an adjusted image ray trace between said given pixel and a given LFSE to intersect said retinal plane at a given adjusted image location, given an estimated direction of a light field emanated by said given pixel given said given LFSE and a modeled redirection of said adjusted image ray trace in accordance with a designated eye focus parameter; associating an adjusted image value designated for said given adjusted image location with said given pixel based on said mapping; rendering each said given pixel according to said adjusted image value associated therewith, thereby rendering a perceptively adjusted version of the input image.

In one embodiment, the retinal plane is angled relative to the digital display.

In one embodiment, the retinal plane is modeled as a function of an input user pupil or eye location that is dynamically acquired via a digitally implemented pupil or eye tracker, wherein said angle between said retinal plane and said digital display is dynamically updated based on data received from said pupil or eye tracker.

In one embodiment, the angle is dynamically updated based on acquired display inclination data.

In one embodiment, the mapping is implemented by scaling the input image on said retinal plane as a function of said designated eye focus parameter.

In one embodiment, the designated eye focus parameter is designated as a function of a quantified abnormal user eye focal length or a corrective eyewear prescription.

In one embodiment, the modeled redirection of said adjusted image ray trace is modelled in accordance with a non-linear eye focus parameter.

In one embodiment, the digital display is defined by a curved surface, and wherein said adjusted image ray trace is computed based on a vector normal to said curved surface for said pixel.

In accordance with another aspect, there is provided a digital display device operable to automatically adjust user perception of an input image to be rendered thereon, the device comprising: a digital display medium comprising an array of pixels and operable to render a pixelated image accordingly; an array of light field shaping elements (LFSE) to shape a light field emanating from at least some of said pixels and thereby at least partially govern a projection thereof from said display medium toward the user; and a hardware processor operable on pixel data for the input image to output adjusted image pixel data to adjust user perception of the input image as rendered by: digitally mapping the input image on a retinal plane of the user; for each given pixel of at least some of said pixels, digitally: projecting an adjusted image ray trace between said given pixel and a given LFSE to intersect said retinal plane at a given adjusted image location, given an estimated direction of a light field emanated by said given pixel given said given LFSE and a modeled redirection of said adjusted image ray trace in accordance with a designated eye focus parameter; associating an adjusted image value designated for said given adjusted image location with said given pixel based on said mapping; rendering each said given pixel according to said adjusted image value associated therewith, thereby rendering a perceptively adjusted version of the input image.

In one embodiment, the retinal plane is angled relative to the digital display.

In one embodiment, the device further comprises a digitally implemented pupil or eye tracker, wherein said retinal plane is modeled as a function of an input user pupil or eye location that is dynamically acquired via said digitally implemented pupil or eye tracker, wherein said angle between said retinal plane and said digital display is dynamically updated based on data received from said pupil or eye tracker.

In one embodiment, the angle is dynamically updated based on acquired display inclination data.

In one embodiment, the mapping is implemented by scaling the input image on said retinal plane as a function of said designated eye focus parameter, wherein said designated eye focus parameter is designated as a function of a quantified abnormal user eye focal length or a corrective eyewear prescription.

In one embodiment, the modeled redirection of said adjusted image ray trace is modelled in accordance with a non-linear eye focus parameter.

In one embodiment, the digital display medium defines a curved surface, and wherein said adjusted image ray trace is computed based on a vector normal to said curved surface for said pixel.

In accordance with another aspect, there is provided a computer-implemented method, automatically implemented by one or more digital processors, to automatically adjust user perception of an input image to be rendered on a digital display via a set of pixels thereof, wherein the digital display has an array of light field shaping elements (LFSE), the method comprising: computing an adjusted image on an adjusted image plane corresponding to a set of display pixel values, said adjusted image being defined as a set of adjusted image pixel values corresponding to a set of image pixels or portions, and wherein: for a trial set of display pixel values derived from said input image: for each given pixel of at least some of said pixels, digitally: calculating a vector between said given pixel and a user pupil location; approximating a direction of a light field emanated by said given pixel based on a given LFSE intersected by said vector; projecting an adjusted image ray trace between said given pixel and said given LFSE to intersect said adjusted image plane at a given adjusted image location given said direction; calculating a beam box region on said adjusted image plane centered on said adjusted image location characterizing the area illuminated by said pixel; identifying one or more image pixels overlapping with said beam box region, and; for each said overlapping image pixels: adding to said image pixel value a pixel value of said display pixel; calculating a cost function value between said adjusted image and said trial input image, said cost function value quantitatively characterizing the difference between said set of image pixel values and said input image; deriving a new set of display pixel values reducing said cost function value; repeating said computing an adjusted image, said calculating a cost function value and said deriving a new set of display pixel values, each time using said new set of display pixel values, until said difference parameter has been minimized; and rendering for each pixel in said set of pixels the corresponding pixel value from said set of display pixel values corresponding to said minimized difference parameter, thereby rendering a perceptively adjusted version of the input image.

In one embodiment, the pixel value is multiplied by a ratio of overlap between said overlapping image pixel and said beam box before being added to said image pixel value.

In one embodiment, the pixel value is multiplied by a relative radiant flux factor.

In one embodiment, the pixel value is multiplied by a pupil transmission factor characterizing how much light from said ray reaches the user's pupil.

In one embodiment, the adjusted image plane is a virtual image plane virtually positioned relative to the digital display at a designated distance from said user pupil location, and wherein said adjusted image ray trace comprises a virtual image vector between said given pixel and said given LFSE to intersect said virtual image plane.

In one embodiment, the adjusted image plane is designated as a user retinal plane, and wherein said adjusted image ray trace is projected to intersect with said user retinal plane by redirecting said adjusted image ray trace given said pupil location in accordance with an input user eye focus aberration parameter.

In one embodiment, the user pupil location is dynamically tracked via a pupil or eye tracker.

In one embodiment, the user perception is adjusted so to at least partially address the user's reduced visual acuity.

In accordance with another aspect, there is provided a non-transitory computer-readable medium comprising digital instructions to be implemented by one or more digital processors to automatically adjust user perception of an input image to be rendered on a digital display via a set of pixels thereof, wherein the digital display has an array of light field shaping elements (LFSE), by: computing an adjusted image on an adjusted image plane corresponding to a set of display pixel values, said adjusted image being defined as a set of adjusted image pixel values corresponding to a set of image pixels or portions, and wherein: for a trial set of display pixel values derived from said input image: for each given pixel of at least some of said pixels, digitally: calculating a vector between said given pixel and a user pupil location; approximating a direction of a light field emanated by said given pixel based on a given LFSE intersected by said vector; projecting an adjusted image ray trace between said given pixel and said given LFSE to intersect said adjusted image plane at a given adjusted image location given said direction; calculating a beam box region on said adjusted image plane centered on said adjusted image location characterizing the area illuminated by said pixel; identifying one or more image pixels overlapping with said beam box region, and; for each said overlapping image pixels: adding to said image pixel value a pixel value of said display pixel; calculating a cost function value between said adjusted image and said trial input image, said cost function value quantitatively characterizing the difference between said set of image pixel values and said input image; deriving a new set of display pixel values reducing said cost function value; repeating said computing an adjusted image, said calculating a cost function value and said deriving a new set of display pixel values, each time using said new set of display pixel values, until said difference parameter has been minimized; and rendering for each pixel in said set of pixels the corresponding pixel value from said set of display pixel values corresponding to said minimized difference parameter, thereby rendering a perceptively adjusted version of the input image.

In one embodiment, the pixel value is multiplied by a ratio of overlap between said overlapping image pixel and said beam box before being added to said image pixel value.

In one embodiment, the pixel value is multiplied by a relative radiant flux factor.

In one embodiment, the adjusted image plane is a virtual image plane virtually positioned relative to the digital display at a designated distance from said user pupil location, and wherein said adjusted image ray trace comprises a virtual image vector between said given pixel and said given LFSE to intersect said virtual image plane.

In one embodiment, the adjusted image plane is designated as a user retinal plane, and wherein said adjusted image ray trace is projected to intersect with said user retinal plane by redirecting said adjusted image ray trace given said pupil location in accordance with an input user eye focus aberration parameter.

In one embodiment, the instructions are further executable to confirm that said adjusted image ray trace intersects with an input pupil area associated with said input user pupil location.

In one embodiment, the user pupil location is dynamically tracked via a pupil or eye tracker.

In one embodiment, the user perception is adjusted so to at least partially address the user's reduced visual acuity.

In accordance with another aspect, there is provided a digital display device operable to automatically adjust user perception of an input image to be rendered thereon, the device comprising: a digital display medium comprising an array of pixels and operable to render a pixelated image accordingly; an array of light field shaping elements (LFSE) to shape a light field emanating from at least some of said pixels and thereby at least partially govern a projection thereof from said display medium toward the user; and a hardware processor operable on pixel data for the input image to output adjusted image pixel data to adjust user perception of the input image as rendered by: computing an adjusted image on an adjusted image plane corresponding to a set of display pixel values, said adjusted image being defined as a set of adjusted image pixel values corresponding to a set of image pixels or portions, and wherein: for a trial set of display pixel values derived from said input image: for each given pixel of at least some of said pixels, digitally: calculating a vector between said given pixel and a user pupil location; approximating a direction of a light field emanated by said given pixel based on a given LFSE intersected by said vector; projecting an adjusted image ray trace between said given pixel and said given LFSE to intersect said adjusted image plane at a given adjusted image location given said direction; calculating a beam box region on said adjusted image plane centered on said adjusted image location characterizing the area illuminated by said pixel; identifying one or more image pixels overlapping with said beam box region, and; for each said overlapping image pixels: adding to said image pixel value a pixel value of said display pixel; calculating a cost function value between said adjusted image and said trial input image, said cost function value quantitatively characterizing the difference between said set of image pixel values and said input image; deriving a new set of display pixel values reducing said cost function value; repeating said computing an adjusted image, said calculating a cost function value and said deriving a new set of display pixel values, each time using said new set of display pixel values, until said difference parameter has been minimized; and rendering for each pixel in said set of pixels the corresponding pixel value from said set of display pixel values corresponding to said minimized difference parameter, thereby rendering a perceptively adjusted version of the input image.

In one embodiment, the pixel value is multiplied by a ratio of overlap between said overlapping image pixel and said beam box before being added to said image pixel value.

In one embodiment, the pixel value is multiplied by a relative radiant flux factor.

In one embodiment, the adjusted image plane is a virtual image plane virtually positioned relative to the digital display at a designated distance from said user pupil location, wherein said adjusted image ray trace comprises a virtual image vector between said given pixel and said given LFSE to intersect said virtual image plane, and wherein said designated distance comprises a minimum viewing distance designated such that said perceptively adjusted version of the input image is adjusted to accommodate a user's reduced visual acuity.

In one embodiment, the device is operable to adjust user perception of the input image for viewing by a viewer having reduced visual acuity such that said perceptively adjusted version of the input image at least partially compensates for the viewer's reduced visual acuity, wherein the device further comprises a user interface for dynamically adjusting said minimum viewing distance.

In one embodiment, the adjusted image plane is designated as a user retinal plane, and wherein said adjusted image ray trace is projected to intersect with said user retinal plane by redirecting said adjusted image ray trace given said pupil location in accordance with an input user eye focus aberration parameter.

In one embodiment, the device further comprises a user interface for dynamically adjusting said input user eye focus aberration parameter.

In one embodiment, the device further comprising a pupil or eye tracker or pupil or eye tracking interface operable to dynamically track and automatically accommodate for changes in said user pupil location.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIGS. 2A and 2B are exploded and side views, respectively, of an assembly of a light field display for an electronic device, in accordance with one embodiment;

FIG. 19 is process flow diagram of an illustrative ray-tracing rendering process, in accordance with another embodiment;

Figure 1:
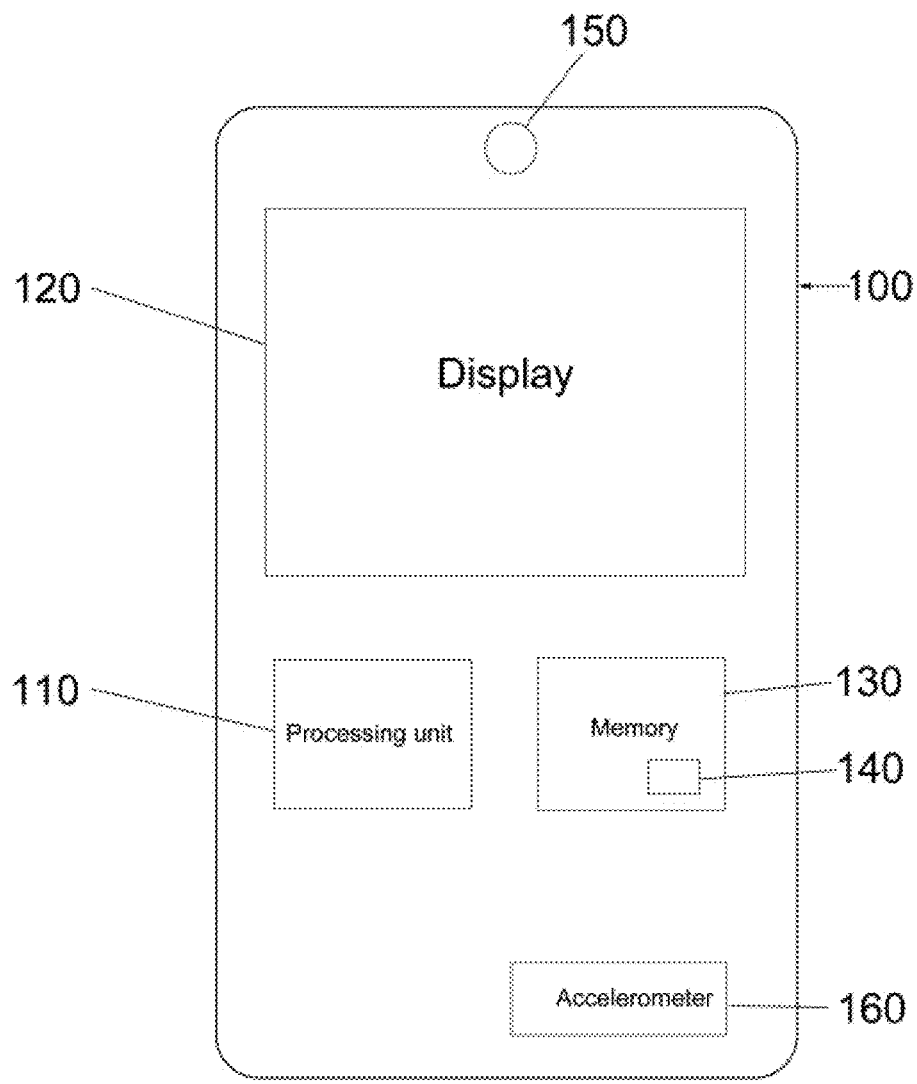
FIG. 1 is a diagrammatical view of an electronic device having a digital display, in accordance with one embodiment.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

The systems and methods described herein provide, in accordance with different embodiments, different examples of a light field display, adjusted pixel rendering method and computer-readable medium therefor, and vision correction system and method using same. For instance, the devices, displays and methods described herein may allow a user's perception of an input image to be displayed, to be adjusted or altered using the light field display. For instance, in some examples, users who would otherwise require corrective eyewear such as glasses or contact lenses, or again bifocals, may consume images produced by such devices, displays and methods in clear or improved focus without the use of such eyewear. Other light field display applications, such as 3D displays and the like, may also benefit from the solutions described herein, and thus, should be considered to fall within the general scope and nature of the present disclosure.

For example, some of the herein described embodiments provide for digital display devices, or devices encompassing such displays, for use by users having reduced visual acuity, whereby images ultimately rendered by such devices can be dynamically processed to accommodate the user's reduced visual acuity so that they may consume rendered images without the use of corrective eyewear, as would otherwise be required. As noted above, embodiments are not to be limited as such as the notions and solutions described herein may also be applied to other technologies in which a user's perception of an input image to be displayed can be altered or adjusted via the light field display.

Generally, digital displays as considered herein will comprise a set of image rendering pixels and a corresponding set of light field shaping elements that at least partially govern a light field emanated thereby to produce a perceptively adjusted version of the input image. In some examples, light field shaping elements may take the form of a light field shaping layer or like array of optical elements to be disposed relative to the display pixels in at least partially governing the emanated light field. As described in further detail below, such light field shaping layer elements may take the form of a microlens and/or pinhole array, or other like arrays of optical elements, or again take the form of an underlying light shaping layer, such as an underlying array of optical gratings or like optical elements operable to produce a directional pixelated output.

Within the context of a light field shaping layer, as described in further detail below in accordance with some embodiments, the light field shaping layer can be disposed at a pre-set distance from the pixelated display so to controllably shape or influence a light field emanating therefrom. For instance, each light field shaping layer can be defined by an array of optical elements centered over a corresponding subset of the display's pixel array to optically influence a light field emanating therefrom and thereby govern a projection thereof from the display medium toward the user, for instance, providing some control over how each pixel or pixel group will be viewed by the viewer's eye(s). As will be further detailed below, arrayed optical elements may include, but are not limited to, lenslets, microlenses or other such diffractive optical elements that together form, for example, a lenslet array; pinholes or like apertures or windows that together form, for example, a parallax or like barrier; concentrically patterned barriers, e.g. cut outs and/or windows, such as a to define a Fresnel zone plate or optical sieve, for example, and that together form a diffractive optical barrier (as described, for example, in Applicant's co-pending U.S. application Ser. No. 15/910,908, the entire contents of which are hereby incorporated herein by reference); and/or a combination thereof, such as for example, a lenslet array whose respective lenses or lenslets are partially shadowed or barrier around a periphery thereof so to combine the refractive properties of the lenslet with some of the advantages provided by a pinhole barrier.

In operation, the display device will also generally invoke a hardware processor operable on image pixel (or subpixel) data for an image to be displayed to output corrected or adjusted image pixel data to be rendered as a function of a stored characteristic of the light field shaping elements and/or layer (e.g. layer distance from display screen, distance between optical elements (pitch), absolute relative location of each pixel or subpixel to a corresponding optical element, properties of the optical elements (size, diffractive and/or refractive properties, etc.), or other such properties, and a selected vision correction or adjustment parameter related to the user's reduced visual acuity or intended viewing experience. While light field display characteristics will generally remain static for a given implementation (i.e. a given shaping element and/or layer will be used and set for each device irrespective of the user), image processing can, in some embodiments, be dynamically adjusted as a function of the user's visual acuity or intended application so to actively adjust a distance of a virtual image plane, or perceived image on the user's retinal plane given a quantified user eye focus or like optical aberration(s), induced upon rendering the corrected/adjusted image pixel data via the static optical layer and/or elements, for example, or otherwise actively adjust image processing parameters as may be considered, for example, when implementing a viewer-adaptive pre-filtering algorithm or like approach (e.g. compressive light field optimization), so to at least in part govern an image perceived by the user's eye(s) given pixel or subpixel-specific light visible thereby through the layer.

Accordingly, a given device may be adapted to compensate for different visual acuity levels and thus accommodate different users and/or uses. For instance, a particular device may be configured to implement and/or render an interactive graphical user interface (GUI) that incorporates a dynamic vision correction scaling function that dynamically adjusts one or more designated vision correction parameter(s) in real-time in response to a designated user interaction therewith via the GUI. For example, a dynamic vision correction scaling function may comprise a graphically rendered scaling function controlled by a (continuous or discrete) user slide motion or like operation, whereby the GUI can be configured to capture and translate a user's given slide motion operation to a corresponding adjustment to the designated vision correction parameter(s) scalable with a degree of the user's given slide motion operation. These and other examples are described in Applicant's co-pending U.S. patent application Ser. No. 15/246,255, the entire contents of which are hereby incorporated herein by reference.

With reference to FIG. 1, and in accordance with one embodiment, a digital display device, generally referred to using the numeral 100, will now be described. In this example, the device 100 is generally depicted as a smartphone or the like, though other devices encompassing a graphical display may equally be considered, such as tablets, e-readers, watches, televisions, GPS devices, laptops, desktop computer monitors, televisions, smart televisions, handheld video game consoles and controllers, vehicular dashboard and/or entertainment displays, and the like.

In the illustrated embodiment, the device 100 comprises a processing unit 110, a digital display 120, and internal memory 130. Display 120 can be an LCD screen, a monitor, a plasma display panel, an LED or OLED screen, or any other type of digital display defined by a set of pixels for rendering a pixelated image or other like media or information. Internal memory 130 can be any form of electronic storage, including a disk drive, optical drive, read-only memory, random-access memory, or flash memory, to name a few examples. For illustrative purposes, memory 130 has stored in it vision correction application 140, though various methods and techniques may be implemented to provide computer-readable code and instructions for execution by the processing unit in order to process pixel data for an image to be rendered in producing corrected pixel data amenable to producing a corrected image accommodating the user's reduced visual acuity (e.g. stored and executable image correction application, tool, utility or engine, etc.). Other components of the electronic device 100 may optionally include, but are not limited to, one or more rear and/or front-facing camera(s) 150, an accelerometer 160 and/or other device positioning/orientation devices capable of determining the tilt and/or orientation of electronic device 100, and the like.

For example, the electronic device 100, or related environment (e.g. within the context of a desktop workstation, vehicular console/dashboard, gaming or e-learning station, multimedia display room, etc.) may include further hardware, firmware and/or software components and/or modules to deliver complementary and/or cooperative features, functions and/or services. For example, in some embodiment, and as will be described in greater detail below, a pupil/eye tracking system may be integrally or cooperatively implemented to improve or enhance corrective image rendering by tracking a location of the user's eye(s)/pupil(s) (e.g. both or one, e.g. dominant, eye(s)) and adjusting light field corrections accordingly. For instance, the device 100 may include, integrated therein or interfacing therewith, one or more eye/pupil tracking light sources, such as one or more infrared (IR) or near-IR (NIR) light source(s) to accommodate operation in limited ambient light conditions, leverage retinal retro-reflections, invoke corneal reflection, and/or other such considerations. For instance, different IR/NIR pupil tracking techniques may employ one or more (e.g. arrayed)

directed or broad illumination light sources to stimulate retinal retro-reflection and/or corneal reflection in identifying a tracking a pupil location. Other techniques may employ ambient or IR/NIR light-based machine vision and facial recognition techniques to otherwise locate and track the user's eye(s)/pupil(s). To do so, one or more corresponding (e.g. visible, IR/NIR) cameras may be deployed to capture eye/pupil tracking signals that can be processed, using various image/sensor data processing techniques, to map a 3D location of the user's eye(s)/pupil(s). In the context of a mobile device, such as a mobile phone, such eye/pupil tracking hardware/software may be integral to the device, for instance, operating in concert with integrated components such as one or more front facing camera(s), onboard IR/NIR light source(s) and the like. In other user environments, such as in a vehicular environment, eye/pupil tracking hardware may be further distributed within the environment, such as dash, console, ceiling, windshield, mirror or similarly-mounted camera(s), light sources, etc.

With reference to FIGS. 2A and 2B, the electronic device 100, such as that illustrated in FIG. 1, is further shown to include a light field shaping layer (LFSL) 200 overlaid atop a display 120 thereof and spaced therefrom via a transparent spacer 310 or other such means as may be readily apparent to the skilled artisan. An optional transparent screen protector 320 is also included atop the layer 200.

For the sake of illustration, the following embodiments will be described within the context of a light field shaping layer defined, at least in part, by a lenslet array comprising an array of microlenses (also interchangeably referred to herein as lenslets) that are each disposed at a distance from a corresponding subset of image rendering pixels in an underlying digital display. It will be appreciated that while a light field shaping layer may be manufactured and disposed as a digital screen overlay, other integrated concepts may also be considered, for example, where light field shaping elements are integrally formed or manufactured within a digital screen's integral components such as a textured or masked glass plate, beam-shaping light sources (e.g. directional light sources and/or backlit integrated optical grating array) or like component.

Accordingly, each lenslet will predictively shape light emanating from these pixel subsets to at least partially govern light rays being projected toward the user by the display device. As noted above, other light field shaping layers may also be considered herein without departing from the general scope and nature of the present disclosure, whereby light field shaping will be understood by the person of ordinary skill in the art to reference measures by which light, that would otherwise emanate indiscriminately (i.e. isotropically) from each pixel group, is deliberately controlled to define predictable light rays that can be traced between the user and the device's pixels through the shaping layer.

For greater clarity, a light field is generally defined as a vector function that describes the amount of light flowing in every direction through every point in space. In other words, anything that produces or reflects light has an associated light field. The embodiments described herein produce light fields from an object that are not "natural" vector functions one would expect to observe from that object. This gives it the ability to emulate the "natural" light fields of objects that do not physically exist, such as a virtual display located far behind the light field display, which will be referred to now as the 'virtual image'. As noted in the examples below, in some embodiments, light field rendering may be adjusted to effectively generate a virtual image on a virtual image plane that is set at a designated distance from an input user pupil location, for example, so to effective push back, or move forward, a perceived image relative to the display device in accommodating a user's reduced visual acuity (e.g. minimum or maximum viewing distance). In yet other embodiments, light field rendering may rather or alternatively seek to map the input image on a retinal plane of the user, taking into account visual aberrations, so to adaptively adjust rendering of the input image on the display device to produce the mapped effect. Namely, where the unadjusted input image would otherwise typically come into focus in front of or behind the retinal plane (and/or be subject to other optical aberrations), this approach allows to map the intended image on the retinal plane and work therefrom to address designated optical aberrations accordingly. Using this approach, the device may further computationally interpret and compute virtual image distances tending toward infinity, for example, for extreme cases of presbyopia. This approach may also more readily allow, as will be appreciated by the below description, for adaptability to other visual aberrations that may not be as readily modeled using a virtual image and image plane implementation. In both of these examples, and like embodiments, the input image is digitally mapped to an adjusted image plane (e.g. virtual image plane or retinal plane) designated to provide the user with a designated image perception adjustment that at least partially addresses designated visual aberrations. Naturally, while visual aberrations may be addressed using these approaches, other visual effects may also be implemented using similar techniques.

Figure 3A:
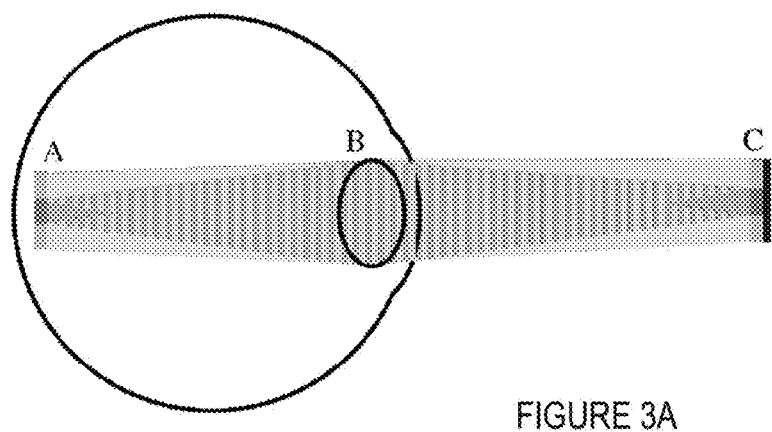
FIGS. 3A, 3B and 3C schematically illustrate normal vision, blurred vision, and corrected vision in accordance with one embodiment, respectively.
Figure 3B:
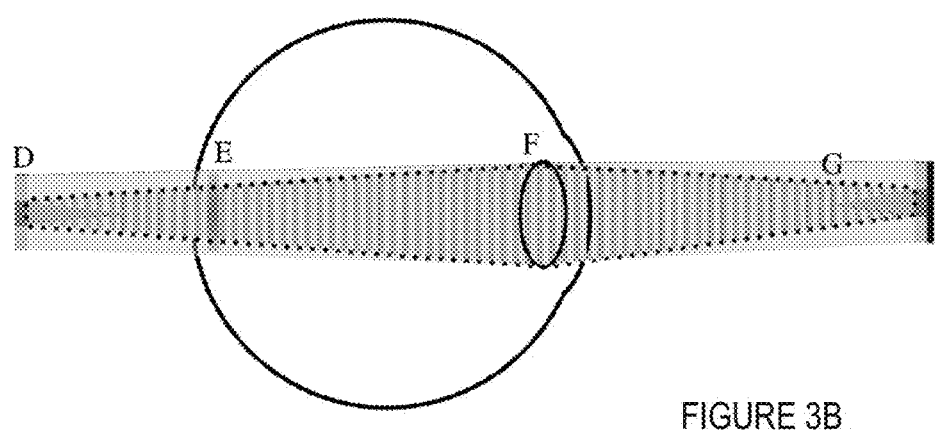

In one example, to apply this technology to vision correction, consider first the normal ability of the lens in an eye, as schematically illustrated in FIG. 3A, where, for normal vision, the image is to the right of the eye (C) and is projected through the lens (B) to the retina at the back of the eye (A). As comparatively shown in FIG. 3B, the poor lens shape (F) in presbyopia causes the image to be focused past the retina (D) forming a blurry image on the retina (E). The dotted lines outline the path of a beam of light (G). Naturally, other visual aberrations can and will have different impacts on image formation on the retina. To address these aberrations, a light field display (K), in accordance with some embodiments, projects the correct sharp image (H) to the back of the retina for an eye with a lens which otherwise could not adjust sufficiently to produce a sharp image. The other two light field pixels (I) and (J) are drawn lightly, but would otherwise fill out the rest of the image.

Figure 3C:
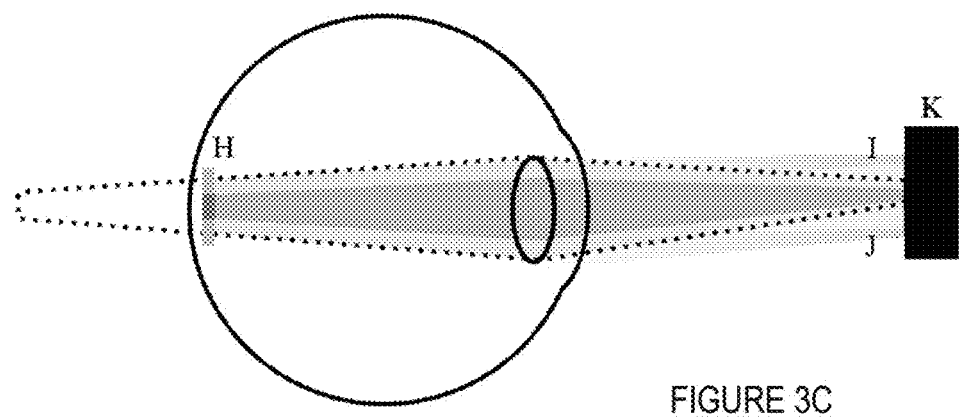

As will be appreciated by the skilled artisan, a light field as seen in FIG. 3C cannot be produced with a 'normal' two-dimensional display because the pixels' light field emits light isotropically. Instead it is necessary to exercise tight control on the angle and origin of the light emitted, for example, using a microlens array or other light field shaping layer such as a parallax barrier, or combination thereof.

Figure 4:
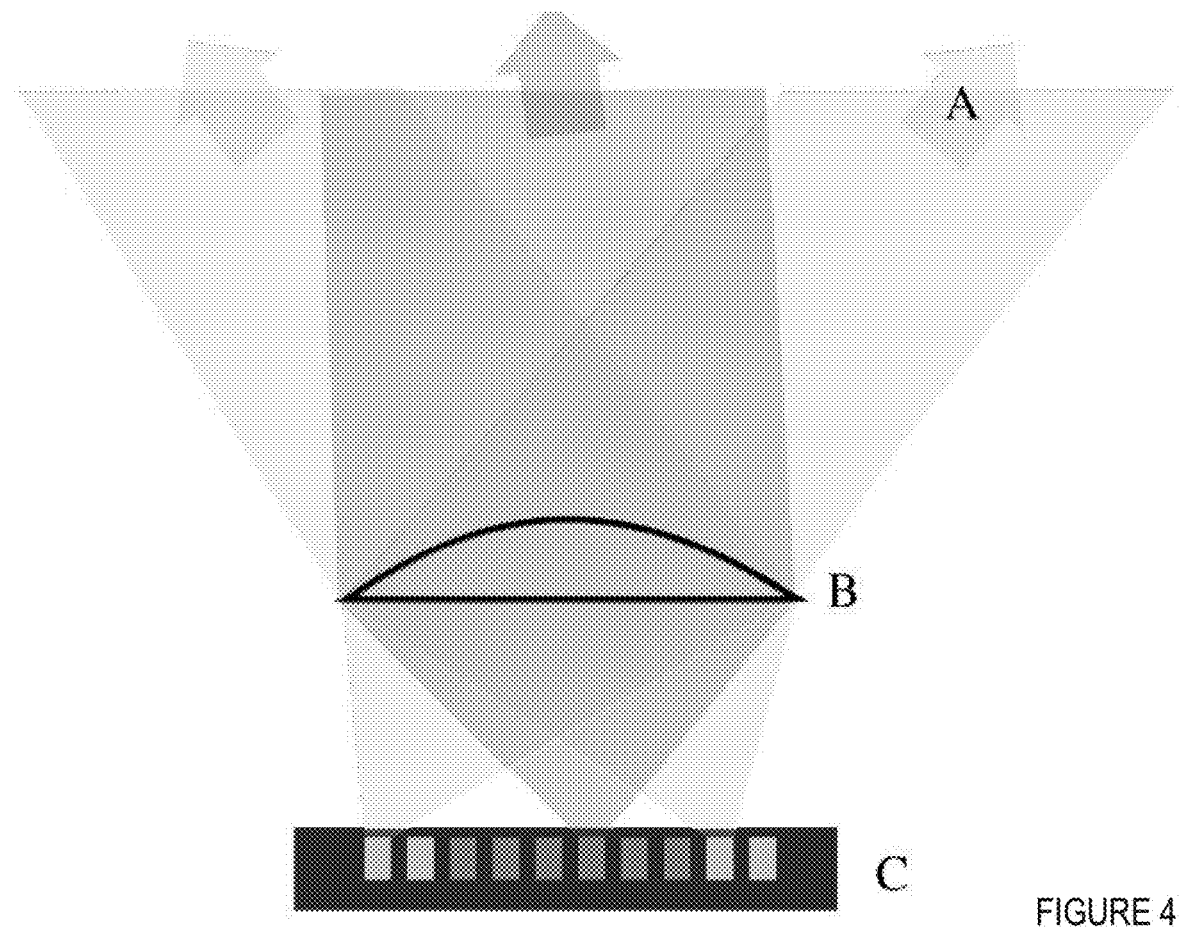
FIG. 4 is a schematic diagram of a single light field pixel defined by a convex lenslet or microlens overlaying an underlying pixel array and disposed at or near its focus to produce a substantially collimated beam, in accordance with one embodiment.

Following with the example of a microlens array, FIG. 4 schematically illustrates a single light field pixel defined by a convex microlens (B) disposed at its focus from a corresponding subset of pixels in an LCD display (C) to produce a substantially collimated beam of light emitted by these pixels, whereby the direction of the beam is controlled by the location of the pixel(s) relative to the microlens. The single light field pixel produces a beam similar to that shown in FIG. 3C where the outside rays are lighter and the majority inside rays are darker. The LCD display (C) emits light which hits the microlens (B) and it results in a beam of substantially collimated light (A).

Figure 5:
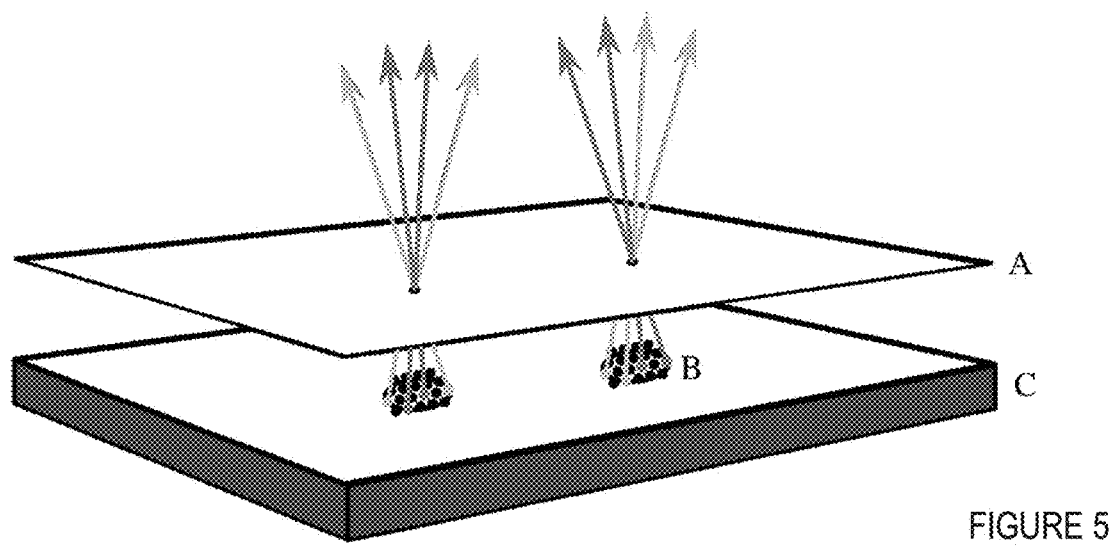
FIG. 5 is another schematic exploded view of an assembly of a light field display in which respective pixel subsets are aligned to emit light through a corresponding microlens or lenslet, in accordance with one embodiment.
Figure 6:
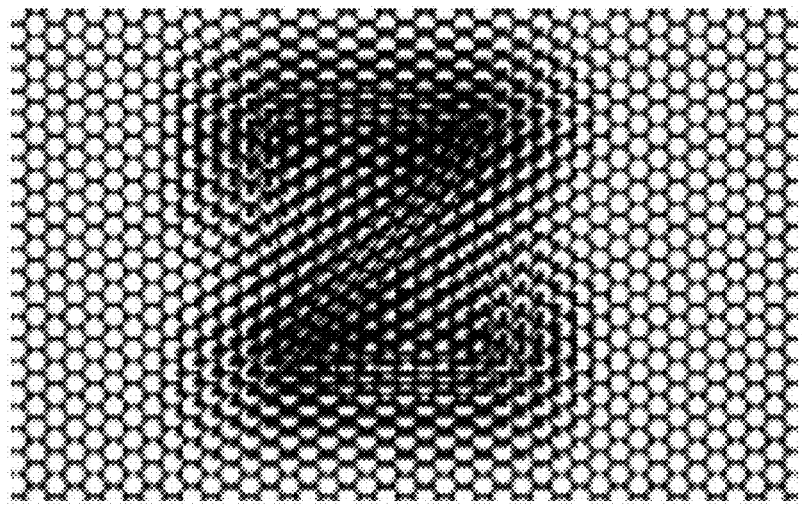
FIG. 6 is an exemplary diagram of a light field pattern that, when properly projected by a light field display, produces a corrected image exhibiting reduced blurring for a viewer having reduced visual acuity, in accordance with one embodiment.

Accordingly, upon predictably aligning a particular microlens array with a pixel array, a designated "circle" of pixels will correspond with each microlens and be responsible for delivering light to the pupil through that lens. FIG. 5 schematically illustrates an example of a light field display assembly in which a microlens array (A) sits above an LCD display on a cellphone (C) to have pixels (B) emit light through the microlens array. A ray-tracing algorithm can thus be used to produce a pattern to be displayed on the pixel array below the microlens in order to create the desired virtual image that will effectively correct for the viewer's reduced visual acuity. FIG. 6 provides an example of such a pattern for the letter "Z". Examples of such ray-tracing algorithms are discussed below.

As will be detailed further below, the separation between the microlens array and the pixel array as well as the pitch of the lenses can be selected as a function of various operating characteristics, such as the normal or average operating distance of the display, and/or normal or average operating ambient light levels.

Further, as producing a light field with angular resolution sufficient for accommodation correction over the full viewing 'zone' of a display would generally require an astronomically high pixel density, instead, a correct light field can be produced, in some embodiments, only at or around the location of the user's pupils. To do so, the light field display can be paired with pupil tracking technology to track a location of the user's eyes/pupils relative to the display. The display can then compensate for the user's eye location and produce the correct virtual image, for example, in real time.

In some embodiments, the light field display can render dynamic images at over 30 frames per second on the hardware in a smartphone.

In some embodiments, the light field display can display a virtual image at optical infinity, meaning that any level of accommodation-based presbyopia (e.g. first order) can be corrected for.

In some further embodiments, the light field display can both push the image back or forward, thus allowing for selective image corrections for both hyperopia (farsightedness) and myopia (nearsightedness).

In order to demonstrate a working light field solution, and in accordance with one embodiment, the following test was set up. A camera was equipped with a simple lens, to simulate the lens in a human eye and the aperture was set to simulate a normal pupil diameter. The lens was focused to 50 cm away and a phone was mounted 25 cm away. This would approximate a user whose minimal seeing distance is 50 cm and is attempting to use a phone at 25 cm.

Figure 7A:
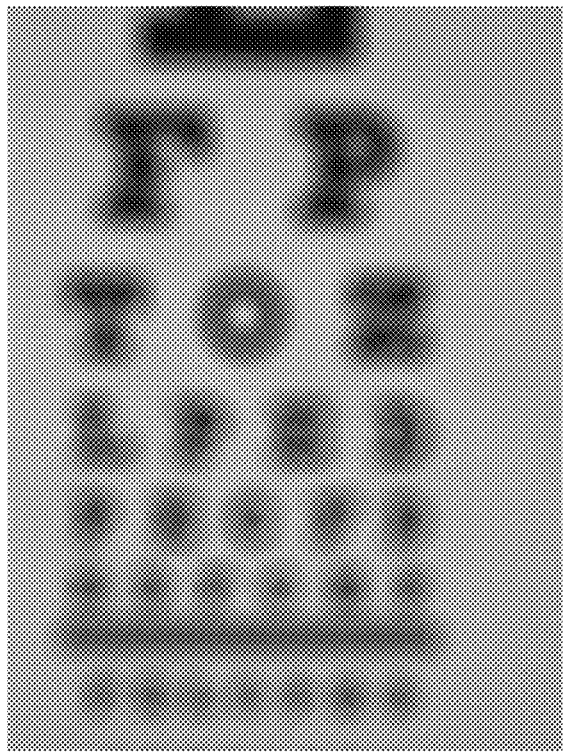
FIGS. 7A and 7B are photographs of a Snellen chart, as illustratively viewed by a viewer with reduced acuity without image correction (blurry image in FIG. 7A) and with image correction via a light field display (corrected image in FIG. 7B), in accordance with one embodiment.
Figure 7B:
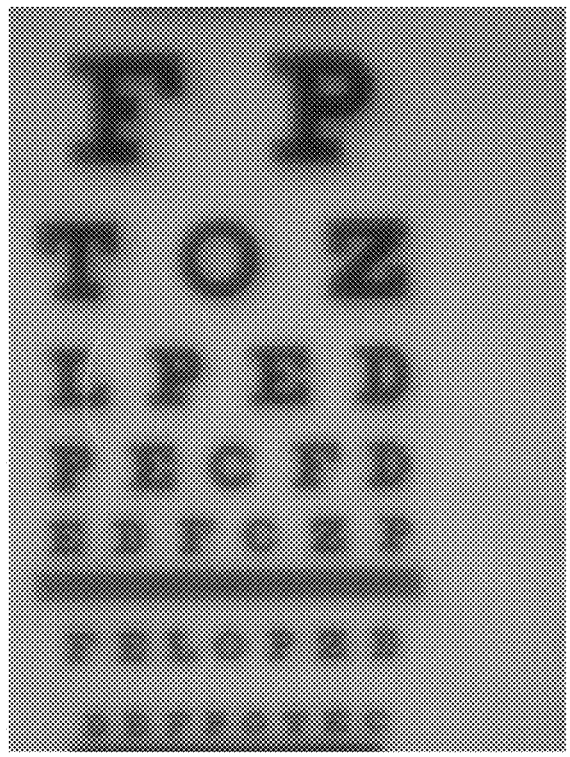

With reading glasses, +2.0 diopters would be necessary for the vision correction. A scaled Snellen chart was displayed on the cellphone and a picture was taken, as shown in FIG. 7A. Using the same cellphone, but with a light field assembly in front that uses that cellphone's pixel array, a virtual image compensating for the lens focus is displayed. A picture was again taken, as shown in FIG. 7B, showing a clear improvement.

Figure 9B:
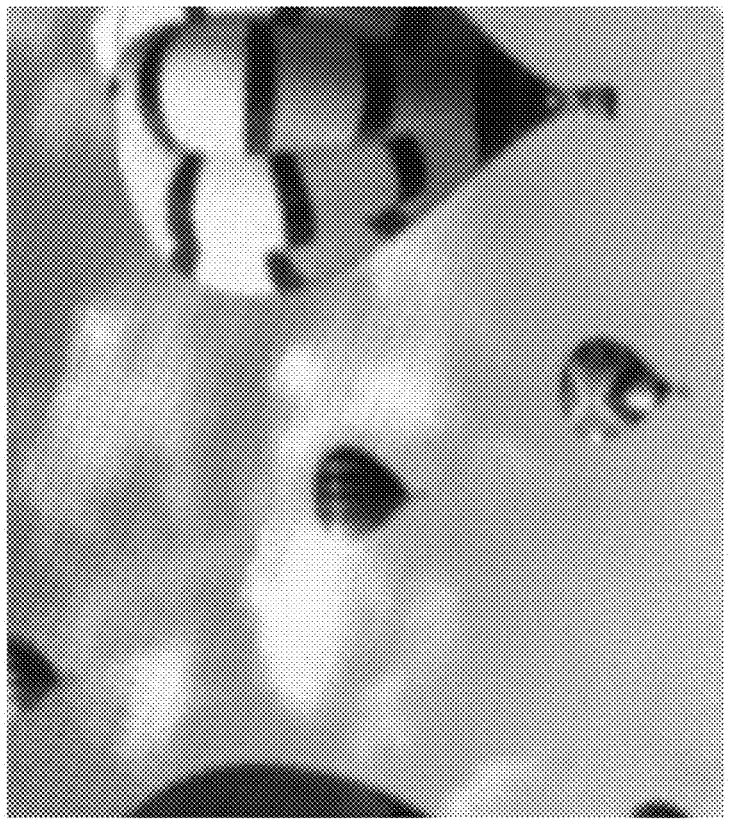
FIGS. 9A and 9B are photographs as illustratively viewed by a viewer with reduced visual acuity without image correction (blurry image in FIG. 9A) and with image correction via a light field display having an angularly mismatched lenslet array (corrected image in FIG. 9B), in accordance with one embodiment.
Figure 9A:
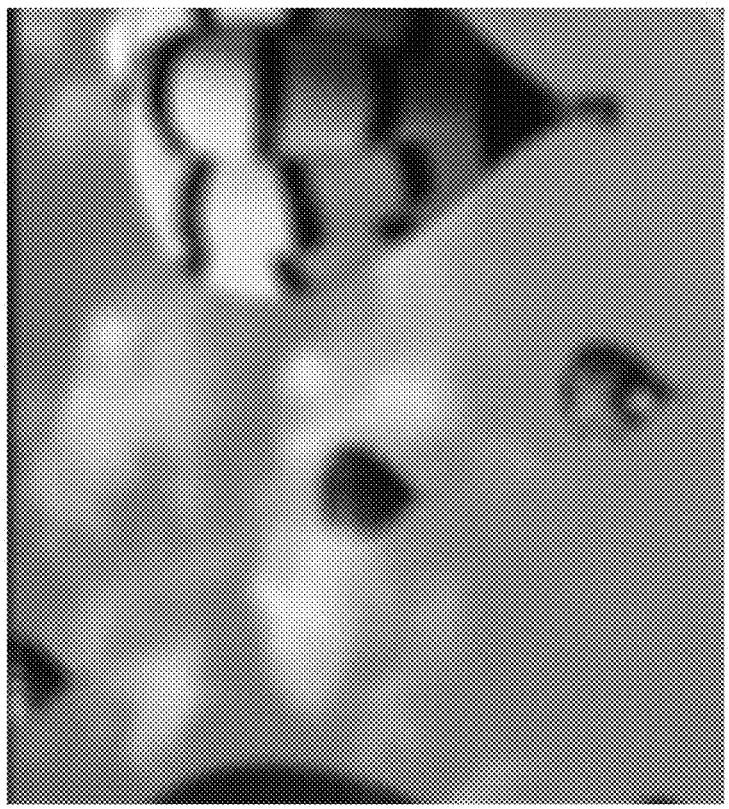

FIGS. 9A and 9B provide another example of results achieved using an exemplary embodiment, in which a colour image was displayed on the LCD display of a Sony™ Xperia™ XZ Premium phone (reported screen resolution of 3840×2160 pixels with 16:9 ratio and approximately 807 pixel-per-inch (ppi) density) without image correction (FIG. 9A) and with image correction through a square fused silica microlens array set at a 2 degree angle relative to the screen's square pixel array and defined by microlenses having a 7.0 mm focus and 200 μm pitch. In this example, the camera lens was again focused at 50 cm with the phone positioned 30 cm away. Another microlens array was used to produce similar results, and consisted of microlenses having a 10.0 mm focus and 150 μm pitch.

Figure 10A:
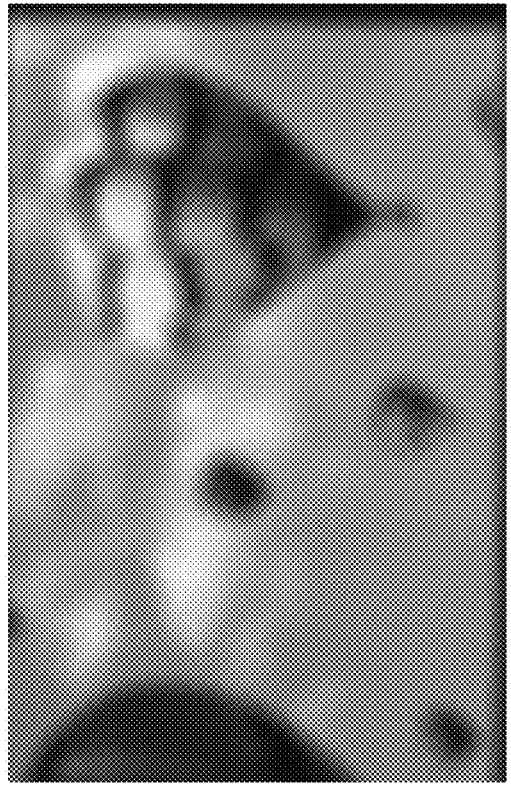
FIGS. 10A and 10B are photographs as illustratively viewed by a viewer with reduced visual acuity without image correction (blurry image in FIG. 10A) and with image correction via a light field display having an angularly mismatched lenslet array (corrected image in FIG. 10B), in accordance with one embodiment.
Figure 10B:
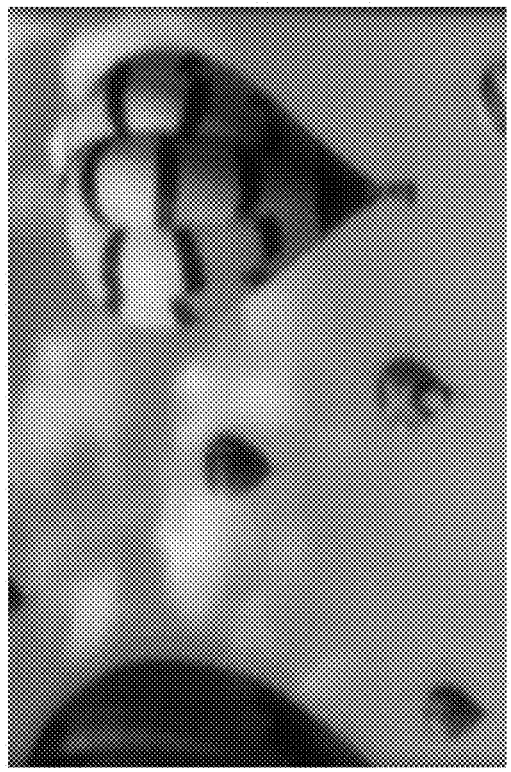

FIGS. 10A and 10B provide yet another example or results achieved using an exemplary embodiment, in which a colour image was displayed on the LCD display of a Sony™ Xperia™ XZ Premium phone without image correction (FIG. 10A) and with image correction through a square fused silica microlens array set at a 2 degree angle relative to the screen's square pixel array and defined by microlenses having a 10.0 mm focus and 150 μm pitch. In this example, the camera lens was focused at 66 cm with the phone positioned 40 cm away.

Accordingly, a display device as described above and further exemplified below, can be configured to render a corrected image via the light field shaping layer that accommodates for the user's visual acuity. By adjusting the image correction in accordance with the user's actual predefined, set or selected visual acuity level, different users and visual acuity may be accommodated using a same device configuration. That is, in one example, by adjusting corrective image pixel data to dynamically adjust a virtual image distance below/above the display as rendered via the light field shaping layer, different visual acuity levels may be accommodated.

As will be appreciated by the skilled artisan, different image processing techniques may be considered, such as those introduced above and taught by Pamplona and/or Huang, for example, which may also influence other light field parameters to achieve appropriate image correction, virtual image resolution, brightness and the like.

Figure 8:
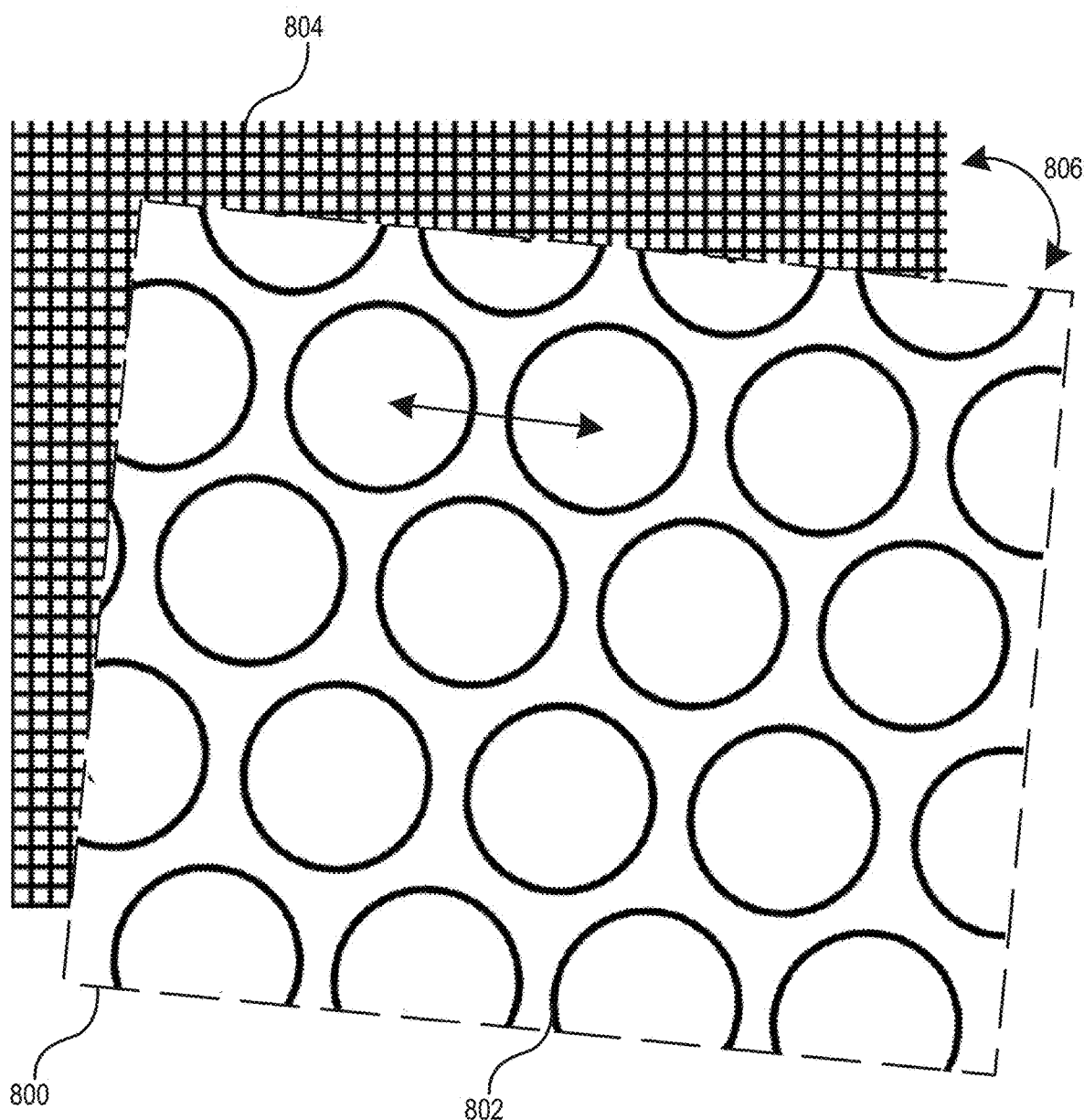
FIG. 8 is a schematic diagram of a portion of a hexagonal lenslet array disposed at an angle relative to an underlying pixel array, in accordance with one embodiment.

With reference to FIG. 8, and in accordance with one embodiment, a microlens array configuration will now be described, in accordance with another embodiment, to provide light field shaping elements in a corrective light field implementation. In this embodiment, the microlens array 800 is defined by a hexagonal array of microlenses 802 disposed so to overlay a corresponding square pixel array 804. In doing so, while each microlens 802 can be aligned with a designated subset of pixels to produce light field pixels as described above, the hexagonal-to-square array mismatch can alleviate certain periodic optical artifacts that may otherwise be manifested given the periodic nature of the optical elements and principles being relied upon to produce the desired optical image corrections. Conversely, a square microlens array may be favoured when operating a digital display comprising a hexagonal pixel array.

In some embodiments, as illustrated in FIG. 8, the microlens array 800 may further or alternatively overlaid at an angle 806 relative to the underlying pixel array, which can further or alternatively alleviate period optical artifacts.

In yet some further or alternative embodiments, a pitch ratio between the microlens array and pixel array may be deliberately selected to further or alternatively alleviate periodic optical artifacts. For example, a perfectly matched pitch ratio (i.e. an exact integer number of display pixels per microlens) is most likely to induce periodic optical artifacts, whereas a pitch ratio mismatch can help reduce such occurrences. Accordingly, in some embodiments, the pitch ratio will be selected to define an irrational number, or at least, an irregular ratio, so to minimize periodic optical artifacts. For instance, a structural periodicity can be defined so to reduce the number of periodic occurrences within the dimensions of the display screen at hand, e.g. ideally selected so to define a structural period that is greater than the size of the display screen being used.

While this example is provided within the context of a microlens array, similar structural design considerations may be applied within the context of a parallax barrier, diffractive barrier or combination thereof.

Figure 11:
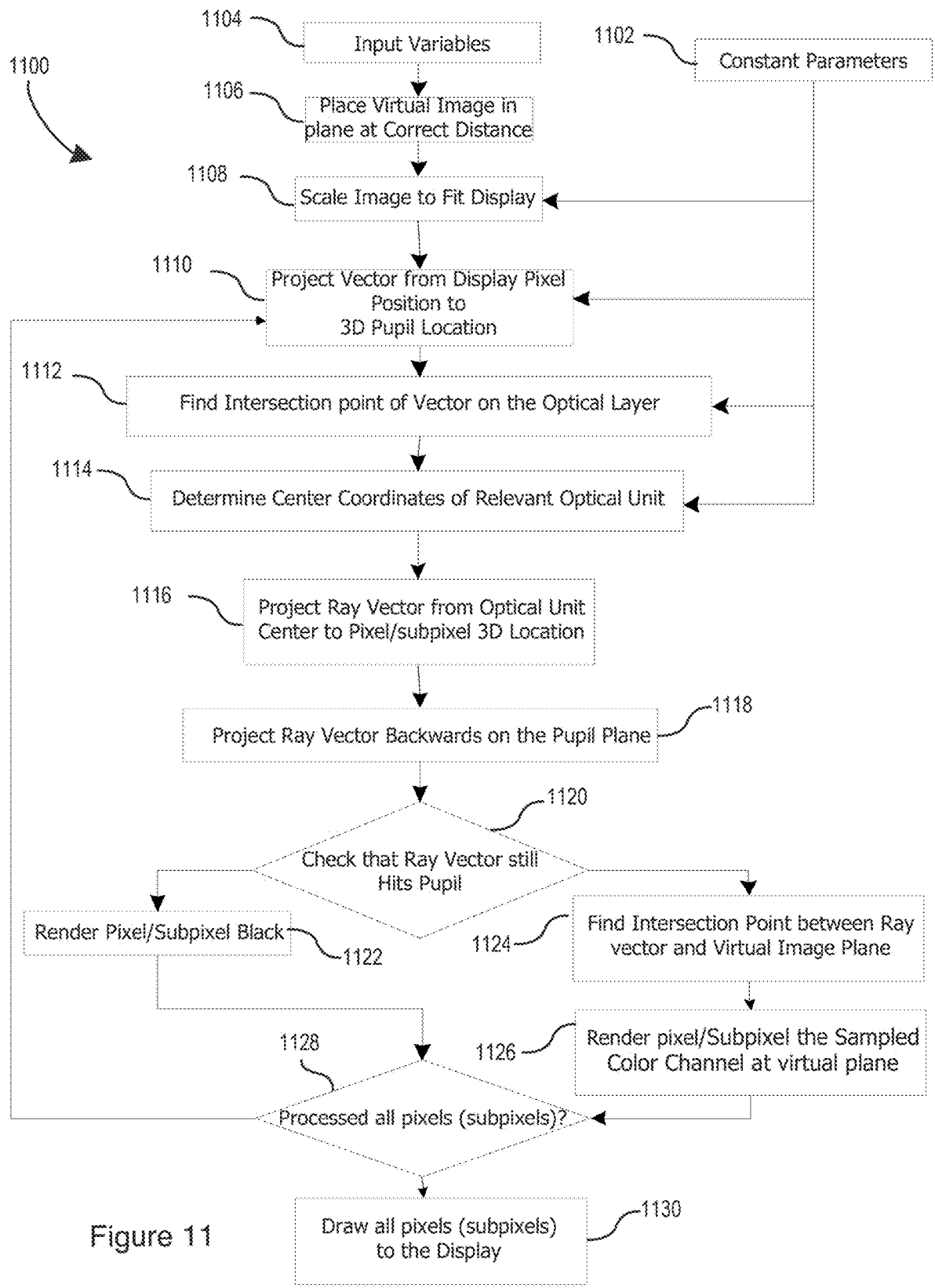
FIG. 11 is a process flow diagram of an illustrative ray-tracing rendering process, in accordance with one embodiment.
Figure 12:
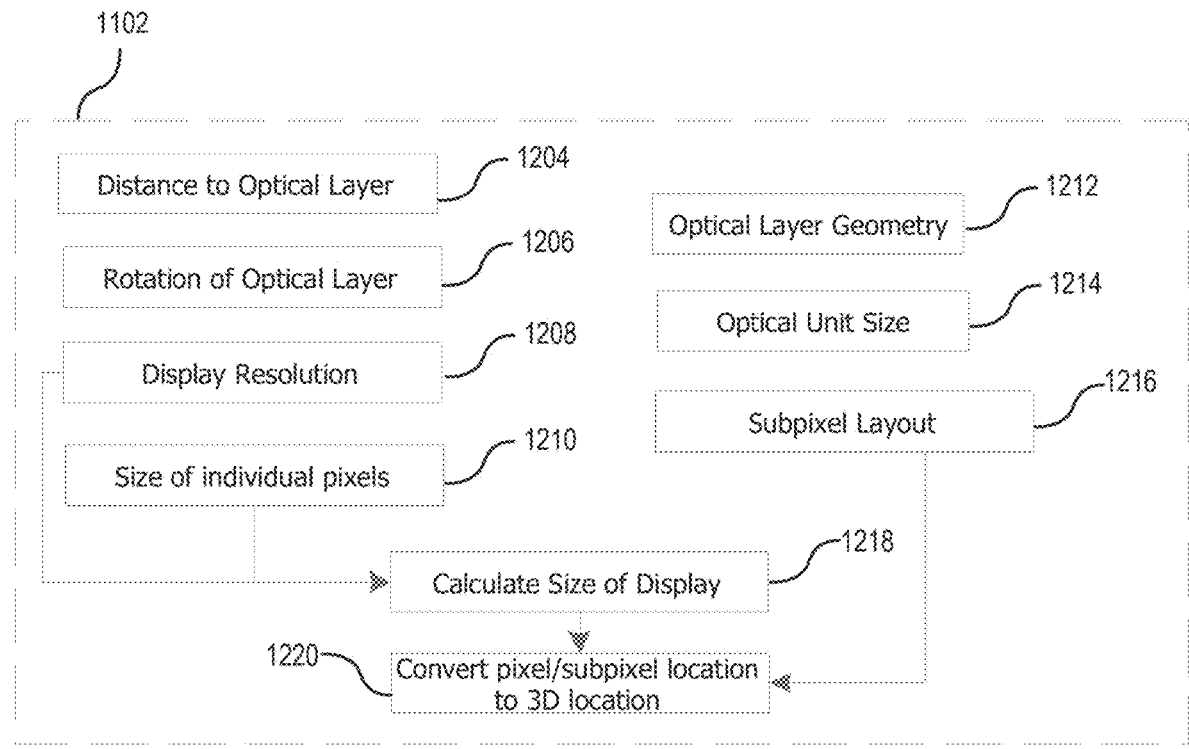
FIGS. 12 and 13 are process flow diagrams of exemplary input constant parameters and variables, respectively, for the ray-tracing rendering process of FIG. 11, in accordance with one embodiment.
Figure 13:
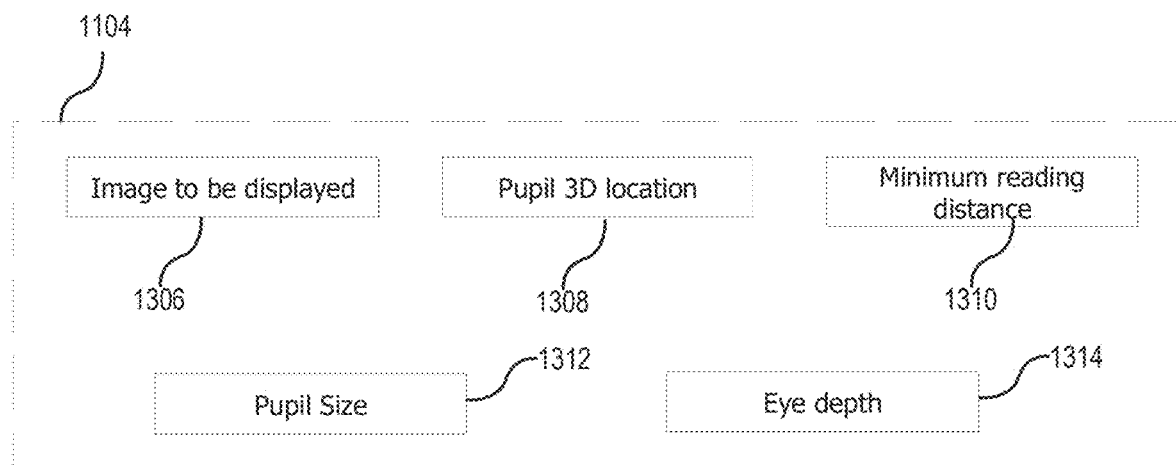

With reference to FIGS. 11 to 13, and in accordance with one embodiment, an exemplary computationally implemented ray-tracing method for rendering a corrected image via an array of light field shaping elements, in this example provided by a light field shaping layer (LFSL) disposed relative to a set of underlying display pixels, that accommodates for the user's reduced visual acuity, will now be described. In this exemplary embodiment, a set of constant parameters 1102 may be pre-determined. These may include, for example, any data that are not expected to significantly change during a user's viewing session, for instance, which are generally based on the physical and functional characteristics of the display for which the method is to be implemented, as will be explained below. Similarly, every iteration of the rendering algorithm may use a set of input variables 1104 which are expected to change either at each rendering iteration or at least between each user's viewing session.

As illustrated in FIG. 12, the list of constant parameters 1102 may include, without limitations, the distance 1204 between the display and the LFSL, the in-plane rotation angle 1206 between the display and LFSL frames of reference, the display resolution 1208, the size of each individual pixel 1210, the optical LFSL geometry 1212, the size of each optical element 1214 within the LFSL and optionally the subpixel layout 1216 of the display. Moreover, both the display resolution 1208 and the size of each individual pixel 1210 may be used to pre-determine both the absolute size of the display in real units (i.e. in mm) and the three-dimensional position of each pixel within the display. In some embodiments where the subpixel layout 1216 is available, the position within the display of each subpixel may also be pre-determined. These three-dimensional location/positions are usually calculated using a given frame of reference located somewhere within the plane of the display, for example a corner or the middle of the display, although other reference points may be chosen. Concerning the optical layer geometry 1212, different geometries may be considered, for example a hexagonal geometry such as the one shown in FIG. 8. Finally, by combining the distance 1204, the rotation angle 1206, and the geometry 1212 with the optical element size 1214, it is possible to similarly pre-determine the three-dimensional location/position of each optical element center with respect to the display's same frame of reference.

FIG. 13 meanwhile illustratively lists an exemplary set of input variables 1104 for method 1100, which may include any input data fed into method 1100 that may reasonably change during a user's single viewing session, and may thus include without limitation: the image(s) to be displayed 1306 (e.g. pixel data such as on/off, colour, brightness, etc.), the three-dimensional pupil location 1308 (e.g. in embodiments implementing active eye/pupil tracking methods) and/or pupil size 1312 and the minimum reading distance 1310 (e.g. one or more parameters representative of the user's reduced visual acuity or condition). In some embodiments, the eye depth 1314 may also be used. The image data 1306, for example, may be representative of one or more digital images to be displayed with the digital pixel display. This image may generally be encoded in any data format used to store digital images known in the art. In some embodiments, images 1306 to be displayed may change at a given framerate.

The pupil location 1308, in one embodiment, is the three-dimensional coordinates of at least one the user's pupils' center with respect to a given reference frame, for example a point on the device or display. This pupil location 1308 may be derived from any eye/pupil tracking method known in the art. In some embodiments, the pupil location 1308 may be determined prior to any new iteration of the rendering algorithm, or in other cases, at a lower framerate. In some embodiments, only the pupil location of a single user's eye may be determined, for example the user's dominant eye (i.e. the one that is primarily relied upon by the user). In some embodiments, this position, and particularly the pupil distance to the screen may otherwise or additionally be rather approximated or adjusted based on other contextual or environmental parameters, such as an average or preset user distance to the screen (e.g. typical reading distance for a given user or group of users; stored, set or adjustable driver distance in a vehicular environment; etc.).

In the illustrated embodiment, the minimum reading distance 1310 is defined as the minimal focus distance for reading that the user's eye(s) may be able to accommodate (i.e. able to view without discomfort). In some embodiments, different values of the minimum reading distance 1310 associated with different users may be entered, for example, as can other adaptive vision correction parameters be considered depending on the application at hand and vision correction being addressed. In some embodiments, minimum reading distance 1310 may be derived from an eye prescription (e.g. glasses prescription or contact prescription) or similar. It may, for example, correspond to the near point distance corresponding to the uncorrected user's eye, which can be calculated from the prescribed corrective lens power assuming that the targeted near point was at 25 cm.

Figure 14A:
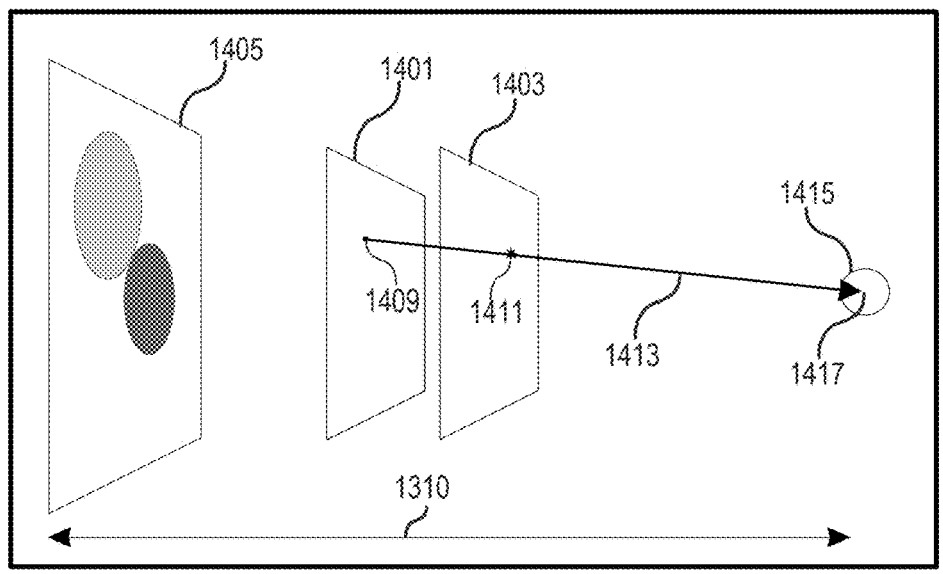
FIGS. 14A to 14C are schematic diagrams illustrating certain process steps of FIG. 11.
Figure 14B:
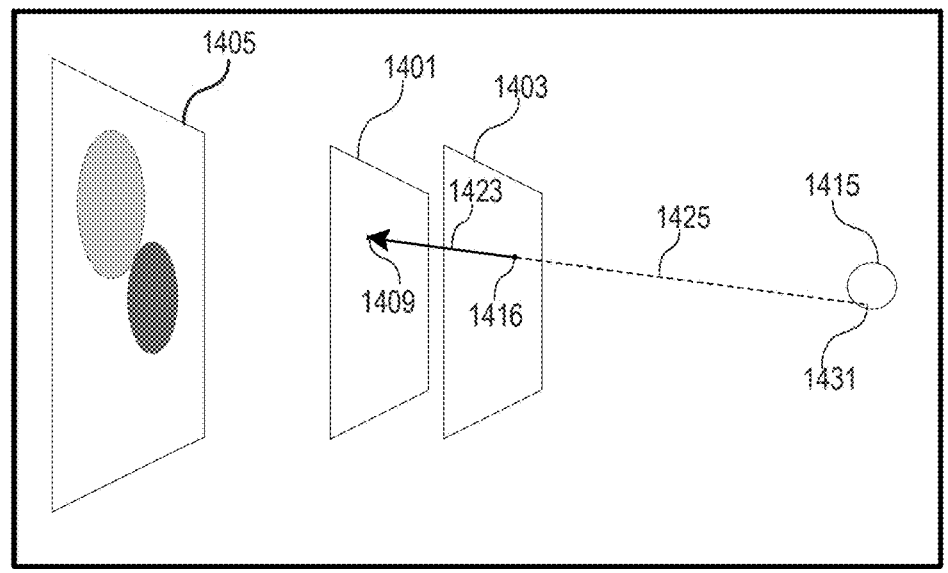
Figure 14C:
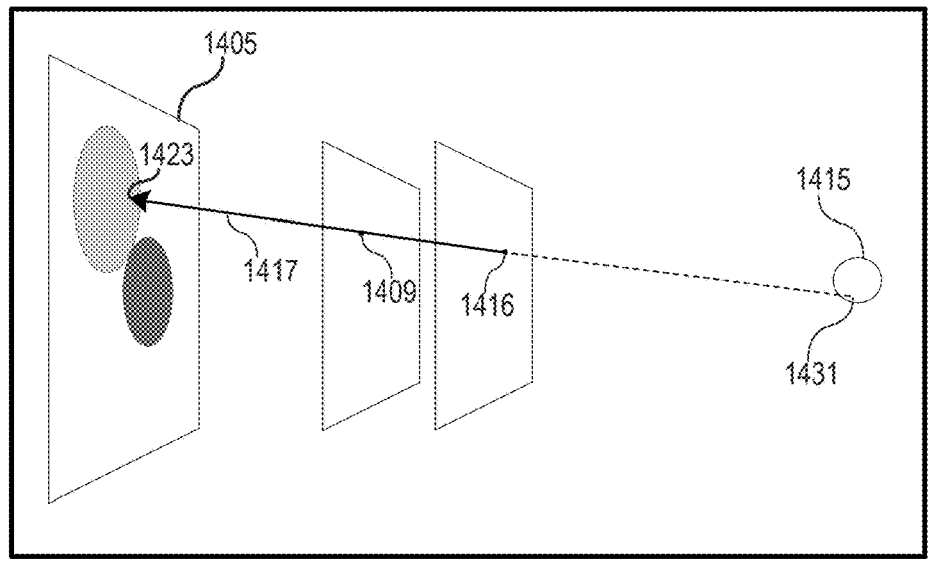

With added reference to FIGS. 14A to 14C, once parameters 1102 and variables 1104 have been set, the method of FIG. 11 then proceeds with step 1106, in which the minimum reading distance 1310 (and/or related parameters) is used to compute the position of a virtual (adjusted) image plane 1405 with respect to the device's display, followed by step 1108 wherein the size of image 1306 is scaled within the image plane 1405 to ensure that it correctly fills the pixel display 1401 when viewed by the distant user. This is illustrated in FIG. 14A, which shows a diagram of the relative positioning of the user's pupil 1415, the light field shaping layer 1403, the pixel display 1401 and the virtual image plane 1405. In this example, the size of image 1306 in image plane 1405 is increased to avoid having the image as perceived by the user appear smaller than the display's size.

An exemplary ray-tracing methodology is described in steps 1110 to 1128 of FIG. 11, at the end of which the output color of each pixel of pixel display 1401 is known so as to virtually reproduce the light field emanating from an image 1306 positioned at the virtual image plane 1405. In FIG. 11, these steps are illustrated in a loop over each pixel in pixel display 1401, so that each of steps 1110 to 1126 describes the computations done for each individual pixel. However, in some embodiments, these computations need not be executed sequentially, but rather, steps 1110 to 1128 may executed in parallel for each pixel or a subset of pixels at the same time. Indeed, as will be discussed below, this exemplary method is well suited to vectorization and implementation on highly parallel processing architectures such as GPUs.

As illustrated in FIG. 14A, in step 1110, for a given pixel 1409 in pixel display 1401, a trial vector 1413 is first generated from the pixel's position to the center position 1417 of pupil 1415. This is followed in step 1112 by calculating the intersection point 1411 of vector 1413 with the LFSL 1403.

The method then finds, in step 1114, the coordinates of the center 1416 of the LFSL optical element closest to intersection point 1411. This step may be computationally intensive and will be discussed in more depth below. Once the position of the center 1416 of the optical element is known, in step 1116, a normalized unit ray vector is generated from drawing and normalizing a vector 1423 drawn from center position 1416 to pixel 1409. This unit ray vector generally approximates the direction of the light field emanating from pixel 1409 through this particular light field element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan. The direction of this ray vector will be used to find the portion of image 1306, and thus the associated color, represented by pixel 1409. But first, in step 1118, this ray vector is projected backwards to the plane of pupil 1415, and then in step 1120, the method verifies that the projected ray vector 1425 is still within pupil 1415 (i.e. that the user can still "see" it). Once the intersection position, for example location 1431 in FIG. 14B, of projected ray vector 1425 with the pupil plane is known, the distance between the pupil center 1417 and the intersection point 1431 may be calculated to determine if the deviation is acceptable, for example by using a pre-determined pupil size and verifying how far the projected ray vector is from the pupil center.

If this deviation is deemed to be too large (i.e. light emanating from pixel 1409 channeled through optical element 1416 is not perceived by pupil 1415), then in step 1122, the method flags pixel 1409 as unnecessary and to simply be turned off or render a black color. Otherwise, as shown in FIG. 14C, in step 1124, the ray vector is projected once more towards virtual image plane 1405 to find the position of the intersection point 1423 on image 1306. Then in step 1126, pixel 1409 is flagged as having the color value associated with the portion of image 1306 at intersection point 1423.

In some embodiments, method 1100 is modified so that at step 1120, instead of having a binary choice between the ray vector hitting the pupil or not, one or more smooth interpolation function (i.e. linear interpolation, Hermite interpolation or similar) are used to quantify how far or how close the intersection point 1431 is to the pupil center 1417 by outputting a corresponding continuous value between 1 or 0. For example, the assigned value is equal to 1 substantially close to pupil center 1417 and gradually change to 0 as the intersection point 1431 substantially approaches the pupil edges or beyond. In this case, the branch containing step 1122 is ignored and step 1220 continues to step 1124. At step 1126, the pixel color value assigned to pixel 1409 is chosen to be somewhere between the full color value of the portion of image 1306 at intersection point 1423 or black, depending on the value of the interpolation function used at step 1120 (1 or 0).

In yet other embodiments, pixels found to illuminate a designated area around the pupil may still be rendered, for example, to produce a buffer zone to accommodate small movements in pupil location, for example, or again, to address potential inaccuracies, misalignments or to create a better user experience.

In some embodiments, steps 1118, 1120 and 1122 may be avoided completely, the method instead going directly from step 1116 to step 1124. In such an exemplary embodiment, no check is made that the ray vector hits the pupil or not, but instead the method assumes that it always does.

Once the output colors of all pixels have been determined, these are finally rendered in step 1130 by pixel display 1401 to be viewed by the user, therefore presenting a light field corrected image. In the case of a single static image, the method may stop here. However, new input variables may be entered and the image may be refreshed at any desired frequency, for example because the user's pupil moves as a function of time and/or because instead of a single image a series of images are displayed at a given framerate.

With reference to FIGS. 19 and 20A to 20D, and in accordance with one embodiment, another exemplary computationally implemented ray-tracing method for rendering an adjusted image via the light field shaping layer (LFSL) that accommodates for the user's reduced visual acuity, for example, will now be described. In this embodiment, the adjusted image portion associated with a given pixel/subpixel is computed (mapped) on the retina plane instead of the virtual image plane considered in the above example, again in order to provide the user with a designated image perception adjustment. Therefore, the currently discussed exemplary embodiment shares some steps with the method of FIG. 11. Indeed, a set of constant parameters 1102 may also be pre-determined. These may include, for example, any data that are not expected to significantly change during a user's viewing session, for instance, which are generally based on the physical and functional characteristics of the display for which the method is to be implemented, as will be explained below. Similarly, every iteration of the rendering algorithm may use a set of input variables 1104 which are expected to change either at each rendering iteration or at least between each user viewing session. The list of possible variables and constants is substantially the same as the one disclosed in FIGS. 12 and 13 and will thus not be replicated here.

Once parameters 1102 and variables 1104 have been set, this second exemplary ray-tracing methodology proceeds from steps 1910 to 1936, at the end of which the output color of each pixel of the pixel display is known so as to virtually reproduce the light field emanating from an image perceived to be positioned at the correct or adjusted image distance, in one example, so to allow the user to properly focus on this adjusted image (i.e. having a focused image projected on the user's retina) despite a quantified visual aberration. In FIG. 19, these steps are illustrated in a loop over each pixel in pixel display 1401, so that each of steps 1910 to 1934 describes the computations done for each individual pixel. However, in some embodiments, these computations need not be executed sequentially, but rather, steps 1910 to 1934 may be executed in parallel for each pixel or a subset of pixels at the same time. Indeed, as will be discussed below, this second exemplary method is also well suited to vectorization and implementation on highly parallel processing architectures such as GPUs.

Referencing once more FIG. 14A, in step 1910 (as in step 1110), for a given pixel in pixel display 1401, a trial vector 1413 is first generated from the pixel's position to pupil center 1417 of the user's pupil 1415. This is followed in step 1912 by calculating the intersection point of vector 1413 with optical layer 1403.

From there, in step 1914, the coordinates of the optical element center 1416 closest to intersection point 1411 are determined. This step may be computationally intensive and will be discussed in more depth below. As shown in FIG. 14B, once the position of the optical element center 1416 is known, in step 1916, a normalized unit ray vector is generated from drawing and normalizing a vector 1423 drawn from optical element center 1416 to pixel 1409. This unit ray vector generally approximates the direction of the light field emanating from pixel 1409 through this particular light field element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan. In step 1918, this ray vector is projected backwards to pupil 1415, and then in step 1920, the method ensures that the projected ray vector 1425 is still within pupil 1415 (i.e. that the user can still "see" it). Once the intersection position, for example location 1431 in FIG. 14B, of projected ray vector 1425 with the pupil plane is known, the distance between the pupil center 1417 and the intersection point 1431 may be calculated to determine if the deviation is acceptable, for example by using a pre-determined pupil size and verifying how far the projected ray vector is from the pupil center.

Now referring to FIGS. 20A to 20D, steps 1921 to 1929 of method 1900 will be described. Once optical element center 1416 of the relevant optical unit has been determined, at step 1921, a vector 2004 is drawn from optical element center 1416 to pupil center 1417. Then, in step 1923, vector 2004 is projected further behind the pupil plane onto focal plane 2006 (location where any light rays originating from optical layer 1403 would be focused by the eye's lens) to locate focus point 2008. For a user with perfect vision, focal plane 2006 would be located at the same location as retina plane 2010, but in this example, focal plane 2006 is located behind retina plane 2006, which would be expected for a user with some form of farsightedness. The position of focal plane 2006 may be derived from the user's minimum reading distance 1310, for example, by deriving therefrom the focal length of the user's eye. Other manually input or computationally or dynamically adjustable means may also or alternatively be considered to quantify this parameter.

The skilled artisan will note that any light ray originating from optical element center 1416, no matter its orientation, will also be focused onto focus point 2008, to a first approximation. Therefore, the location on retina plane (2012) onto which light entering the pupil at intersection point 1431 will converge may be approximated by drawing a straight line between intersection point 1431 where ray vector 1425 hits the pupil 1415 and focus point 2008 on focal plane 2006. The intersection of this line with retina plane 2010 (retina image point 2012) is thus the location on the user's retina corresponding to the image portion that will be reproduced by corresponding pixel 1409 as perceived by the user. Therefore, by comparing the relative position of retina point 2012 with the overall position of the projected image on the retina plane 2010, the relevant adjusted image portion associated with pixel 1409 may be computed.

To do so, at step 1927, the corresponding projected image center position on retina plane 2010 is calculated. Vector 2016 is generated originating from the center position of display 1401 (display center position 2018) and passing through pupil center 1417. Vector 2016 is projected beyond the pupil plane onto retina plane 2010, wherein the associated intersection point gives the location of the corresponding retina image center 2020 on retina plane 2010. The skilled technician will understand that step 1927 could be performed at any moment prior to step 1929, once the relative pupil center location 1417 is known in input variables step 1904. Once image center 2020 is known, one can then find the corresponding image portion of the selected pixel/subpixel at step 1929 by calculating the x/y coordinates of retina image point 2012 relative to retina image center 2020 on the retina, scaled to the x/y retina image size 2031.

Figure 20A:
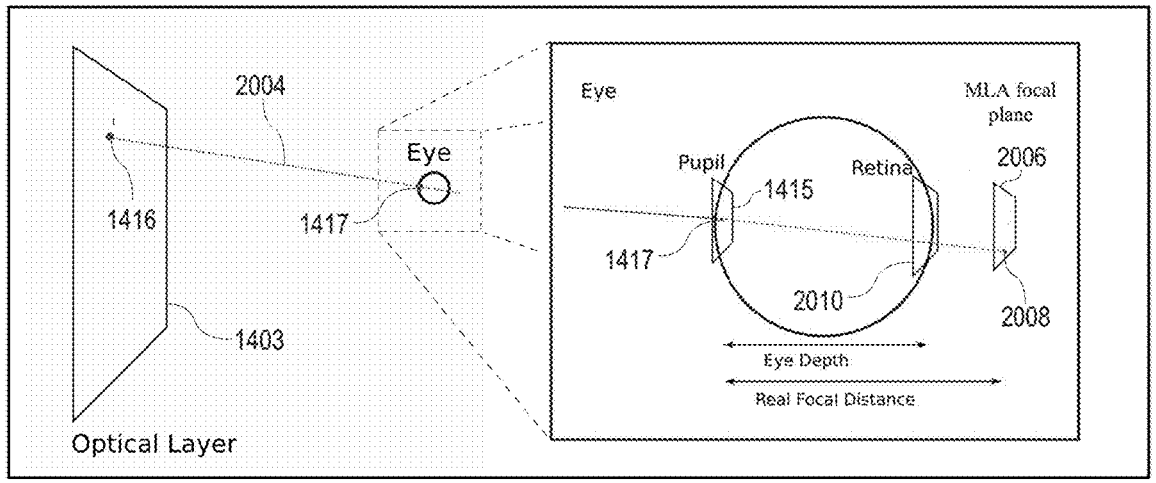
FIGS. 20A to 20D are schematic diagrams illustrating certain process steps of FIG. 19.
Figure 20B:
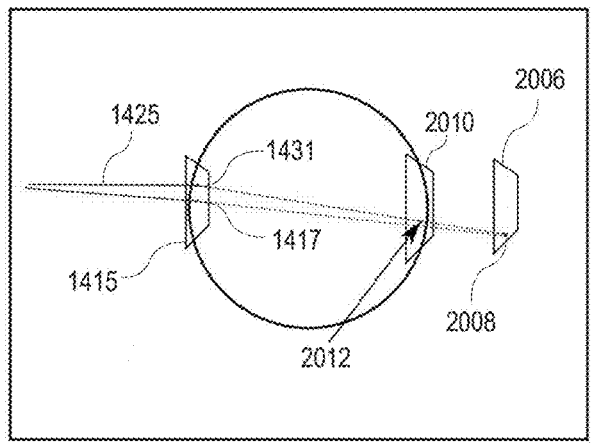
Figure 20C:
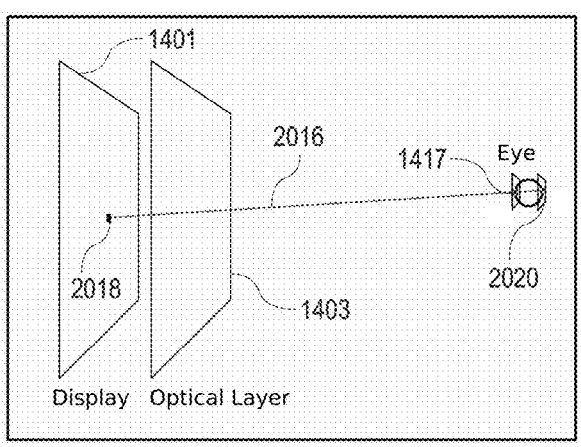
Figure 20D:
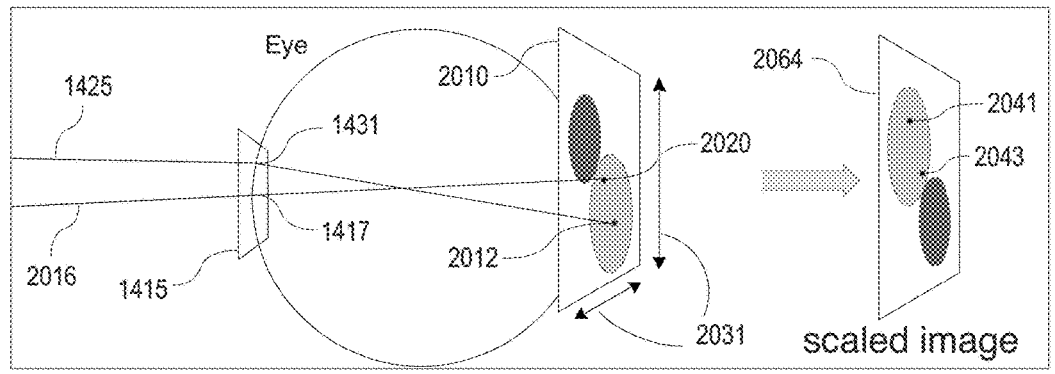

This retina image size 2031 may be computed by calculating the magnification of an individual pixel on retina plane 2010, for example, which may be approximately equal to the x or y dimension of an individual pixel multiplied by the eye depth 1314 and divided by the absolute value of the distance to the eye (i.e. the magnification of pixel image size from the eye lens). Similarly, for comparison purposes, the input image is also scaled by the image x/y dimensions to produce a corresponding scaled input image 2064. Both the scaled input image and scaled retina image should have a width and height between −0.5 to 0.5 units, enabling a direct comparison between a point on the scaled retina image 2010 and the corresponding scaled input image 2064, as shown in FIG. 20D.

From there, the image portion position 2041 relative to retina image center position 2043 in the scaled coordinates (scaled input image 2064) corresponds to the inverse (because the image on the retina is inverted) scaled coordinates of retina image point 2012 with respect to retina image center 2020. The associated color with image portion position 2041 is therefrom extracted and associated with pixel 1409.

In some embodiments, method 1900 may be modified so that at step 1920, instead of having a binary choice between the ray vector hitting the pupil or not, one or more smooth interpolation function (i.e. linear interpolation, Hermite interpolation or similar) are used to quantify how far or how close the intersection point 1431 is to the pupil center 1417 by outputting a corresponding continuous value between 1 or 0. For example, the assigned value is equal to 1 substantially close to pupil center 1417 and gradually change to 0 as the intersection point 1431 substantially approaches the pupil edges or beyond. In this case, the branch containing step 1122 is ignored and step 1920 continues to step 1124. At step 1931, the pixel color value assigned to pixel 1409 is chosen to be somewhere between the full color value of the portion of image 1306 at intersection point 1423 or black, depending on the value of the interpolation function used at step 1920 (1 or 0).

In yet other embodiments, pixels found to illuminate a designated area around the pupil may still be rendered, for example, to produce a buffer zone to accommodate small movements in pupil location, for example, or again, to address potential inaccuracies or misalignments.

Once the output colors of all pixels in the display have been determined (check at step 1934 is true), these are finally rendered in step 1936 by pixel display 1401 to be viewed by the user, therefore presenting a light field corrected image. In the case of a single static image, the method may stop here. However, new input variables may be entered and the image may be refreshed at any desired frequency, for example because the user's pupil moves as a function of time and/or because instead of a single image a series of images are displayed at a given framerate.

As will be appreciated by the skilled artisan, selection of the adjusted image plane onto which to map the input image in order to adjust a user perception of this input image allows for different ray tracing approaches to solving a similar challenge, that is of creating an adjusted image using the light field display that can provide an adjusted user perception, such as addressing a user's reduce visual acuity. While mapping the input image to a virtual image plane set at a designated minimum (or maximum) comfortable viewing distance can provide one solution, the alternate solution may allow accommodation of different or possibly more extreme visual aberrations. For example, where a virtual image is ideally pushed to infinity (or effectively so), computation of an infinite distance becomes problematic. However, by designating the adjusted image plane as the retinal plane, the illustrative process of FIG. 19 can accommodate the formation of a virtual image effectively set at infinity without invoking such computational challenges. Likewise, while first order focal length aberrations are illustratively described with reference to FIG. 19, higher order or other optical anomalies may be considered within the present context, whereby a desired retinal image is mapped out and traced while accounting for the user's optical aberration(s) so to compute adjusted pixel data to be rendered in producing that image. These and other such considerations should be readily apparent to the skilled artisan.

While the computations involved in the above described ray-tracing algorithms (steps 1110 to 1128 of FIG. 11 or steps 1920 to 1934 of FIG. 19) may be done on general CPUs, it may be advantageous to use highly parallel programming schemes to speed up such computations. While in some embodiments, standard parallel programming libraries such as Message Passing Interface (MPI) or OPENMP may be used to accelerate the light field rendering via a general-purpose CPU, the light field computations described above are especially tailored to take advantage of graphical processing units (GPU), which are specifically tailored for massively parallel computations. Indeed, modern GPU chips are characterized by the very large number of processing cores, and an instruction set that is commonly optimized for graphics. In typical use, each core is dedicated to a small neighborhood of pixel values within an image, e.g., to perform processing that applies a visual effect, such as shading, fog, affine transformation, etc. GPUs are usually also optimized to accelerate exchange of image data between such processing cores and associated memory, such as RGB frame buffers. Furthermore, smartphones are increasingly being equipped with powerful GPUs to speed the rendering of complex screen displays, e.g., for gaming, video, and other image-intensive applications. Several programming frameworks and languages tailored for programming on GPUs include, but are not limited to, CUDA, OpenCL, OpenGL Shader Language (GLSL), High-Level Shader Language (HLSL) or similar. However, using GPUs efficiently may be challenging and thus require creative steps to leverage their capabilities, as will be discussed below.

With reference to FIGS. 15 to 18C and in accordance with one exemplary embodiment, an exemplary process for computing the center position of an associated light field shaping element in the ray-tracing process of FIG. 11 (or FIG. 19) will now be described. The series of steps are specifically tailored to avoid code branching, so as to be increasingly efficient when run on GPUs (i.e. to avoid so called "warp divergence"). Indeed, with GPUs, because all the processors must execute identical instructions, divergent branching can result in reduced performance.

Figure 15:
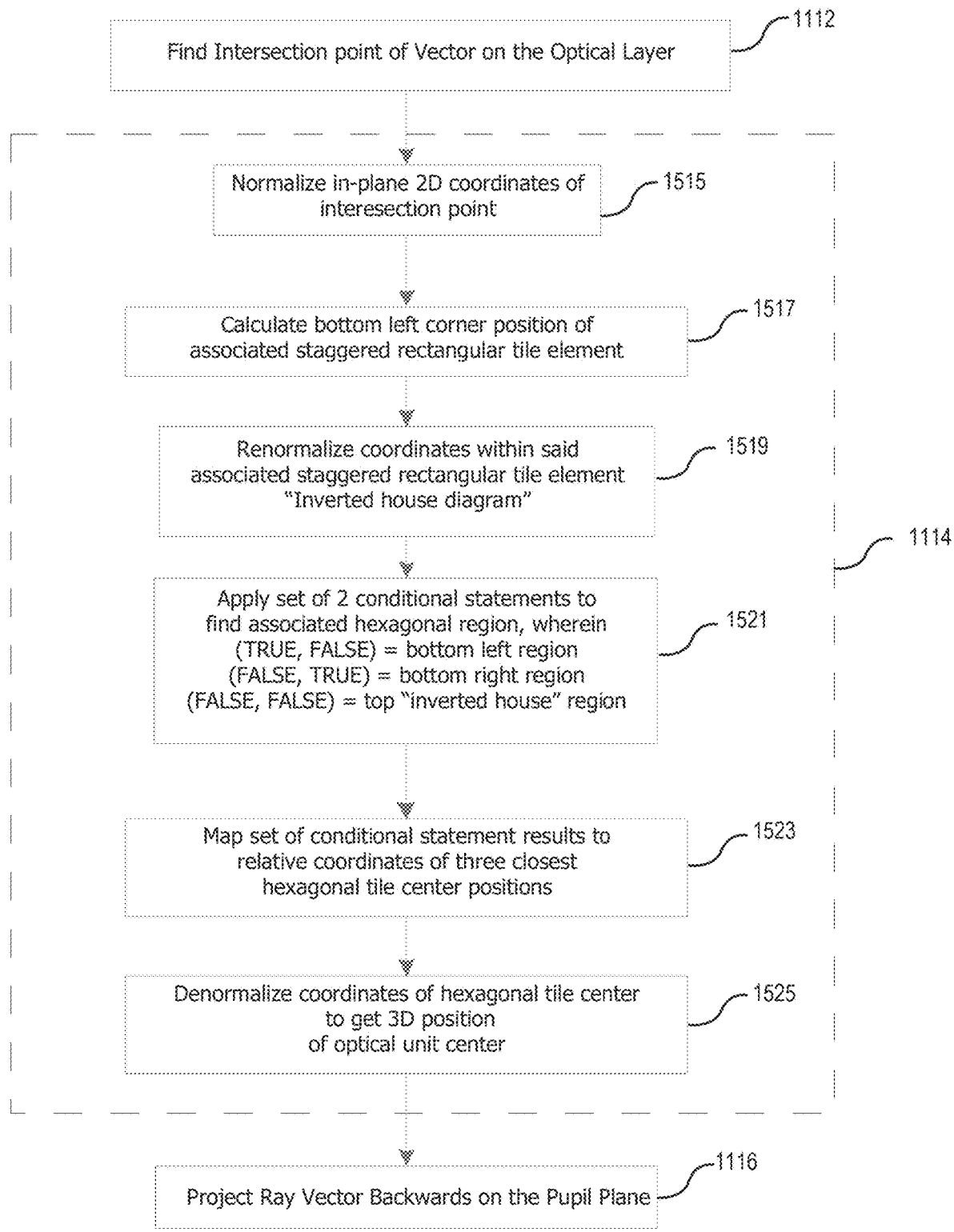
FIG. 15 is a process flow diagram of an exemplary process for computing the center position of an associated light field shaping unit in the ray-tracing rendering process of FIG. 11, in accordance with one embodiment.

With reference to FIG. 15, and in accordance with one embodiment, step 1114 of FIG. 11 is expanded to include steps 1515 to 1525. A similar discussion can readily be made in respect of step 1914 of FIG. 19, and thus need not be explicitly detailed herein. The method receives from step 1112 the 2D coordinates of the intersection point 1411 (illustrated in FIG. 14A) of the trial vector 1413 with optical layer 1403. As discussed with respect to the exemplary embodiment of FIG. 8, there may be a difference in orientation between the frames of reference of the optical layer (hexagonal array of microlenses 802 in FIG. 8, for example) and of the corresponding pixel display (square pixel array 804 in FIG. 8, for example). This is why, in step 1515, these input intersection coordinates, which are initially calculated from the display's frame of reference, may first be rotated to be expressed from the light field shaping layer's frame of reference and optionally normalized so that each individual light shaping element has a width and height of 1 unit. The following description will be equally applicable to any light field shaping layer having a hexagonal geometry like the exemplary embodiment of FIG. 8. Note however that the method steps 1515 to 1525 described herein may be equally applied to any kind of light field shaping layer sharing the same geometry (i.e. not only a microlens array, but pinhole arrays as well, etc.). Likewise, while the following example is specific to an exemplary hexagonal array of LFSL elements definable by a hexagonal tile array of regular hexagonal tiles, other geometries may also benefit from some or all of the features and/or advantages of the herein-described and illustrated embodiments. For example, different hexagonal LFSL element arrays, such as stretched/elongated, skewed and/or rotated arrays may be considered, as can other nestled array geometries in which adjacent rows and/or columns of the LFSL array at least partially "overlap" or inter-nest. For instance, as will be described further below, hexagonal arrays and like nestled array geometries will generally provide for a commensurately sized rectangular/square tile of an overlaid rectangular/square array or grid to naturally encompass distinct regions as defined by two or more adjacent underlying nestled array tiles, which can be used to advantage in the examples provided below. In yet other embodiments, the processes discussed herein may be applied to rectangular and/or square LFSL element arrays. Other LFSL element array geometries may also be considered, as will be appreciated by the skilled artisan upon reading of the following example, without departing from the general scope and nature of the present disclosure.

Figure 16A:
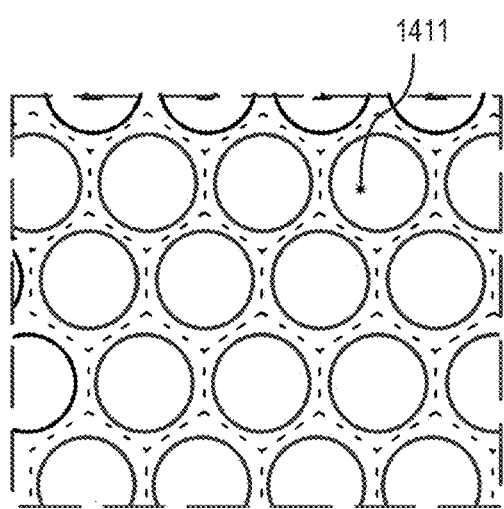
FIGS. 16A and 16B are schematic diagrams illustrating an exemplary hexagonal light field shaping layer with a corresponding hexagonal tile array, in accordance with one embodiment.
Figure 16B:
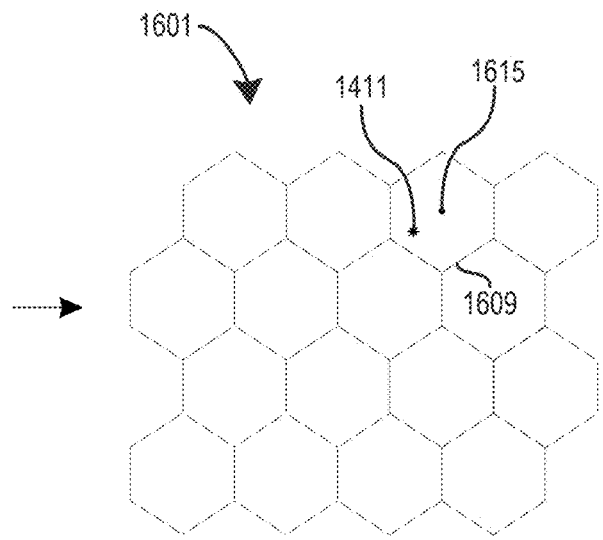

For hexagonal geometries, as illustrated in FIGS. 16A and 16B, the hexagonal symmetry of the light field shaping layer 1403 may be represented by drawing an array of hexagonal tiles 1601, each centered on their respective light field shaping element, so that the center of a hexagonal tile element is more or less exactly the same as the center position of its associated light field shaping element. Thus, the original problem is translated to a slightly similar one whereby one now needs to find the center position 1615 of the associated hexagonal tile 1609 closest to the intersection point 1411, as shown in FIG. 16B.

Figure 17A:
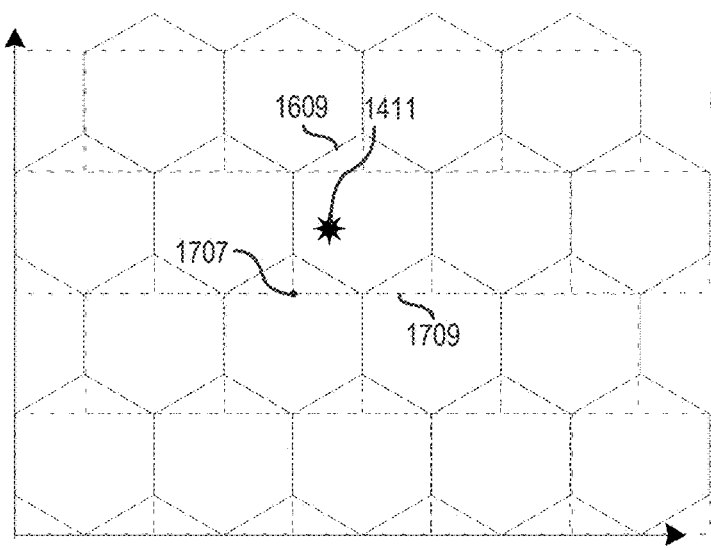
FIGS. 17A and 17B are schematic diagrams illustrating overlaying a staggered rectangular tile array over the hexagonal tile array of FIGS. 16A and 16B, in accordance with one embodiment.

To solve this problem, the array of hexagonal tiles 1601 may be superimposed on or by a second array of staggered rectangular tiles 1705, in such a way as to make an "inverted house" diagram within each rectangle, as clearly illustrated in FIG. 17A, namely defining three linearly segregated tile regions for each rectangular tile, one region predominantly associated with a main underlying hexagonal tile, and two other opposed triangular regions associated with adjacent underlying hexagonal tiles. In doing so, the nestled hexagonal tile geometry is translated to a rectangular tile geometry having distinct linearly segregated tile regions defined therein by the edges of underlying adjacently disposed hexagonal tiles. Again, while regular hexagons are used to represent the generally nestled hexagonal LFSL element array geometry, other nestled tile geometries may be used to represent different nestled element geometries. Likewise, while a nestled array is shown in this example, different staggered or aligned geometries may also be used, in some examples, in some respects, with reduced complexity, as further described below.

Furthermore, while this particular example encompasses the definition of linearly defined tile region boundaries, other boundary types may also be considered provided they are amenable to the definition of one or more conditional statements, as illustrated below, that can be used to output a corresponding set of binary or Boolean values that distinctly identify a location of a given point within one or another of these regions, for instance, without invoking, or by limiting, processing demands common to branching or looping decision logics/trees/statements/etc.

Figure 17B:
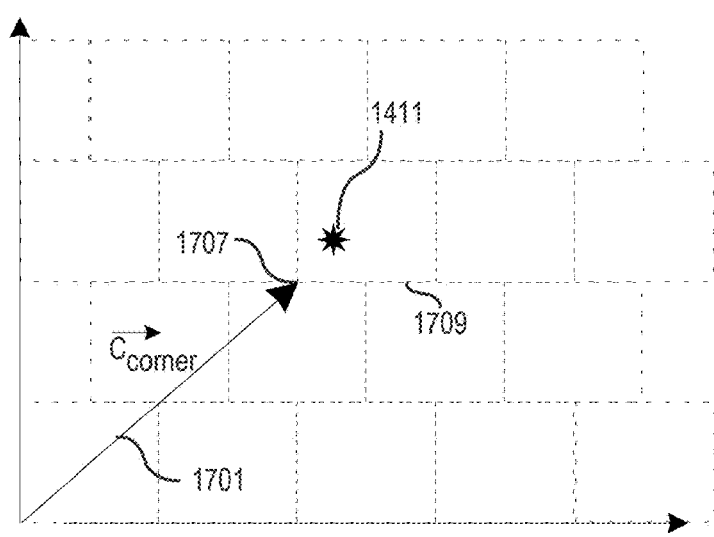

Following with hexagonal example, to locate the associated hexagon tile center 1615 closest to the intersection point 1411, in step 1517, the method first computes the 2D position of the bottom left corner 1705 of the associated (normalized) rectangular tile element 1609 containing intersection point 1411, as shown in FIG. 17B. The position of the bottom left corner of the hexagon containing the intersection point 1411 can be calculated without using any branching statements by the following two equations (here in normalized coordinates wherein each rectangle has a height and width of one unit):

$$\vec{t} = (\text{floor}(uv_y), 0)$$

$$\vec{C}_{corner} = (\vec{uv} + \vec{t}) - \vec{t}$$

where $\vec{uv}$ is the position vector of intersection point 1411 in the common frame of reference of the hexagonal and staggered rectangular tile arrays, and the floor( ) function returns the greatest integer less than or equal to each of the xy coordinates of $\vec{uv}$.

Figure 18A:
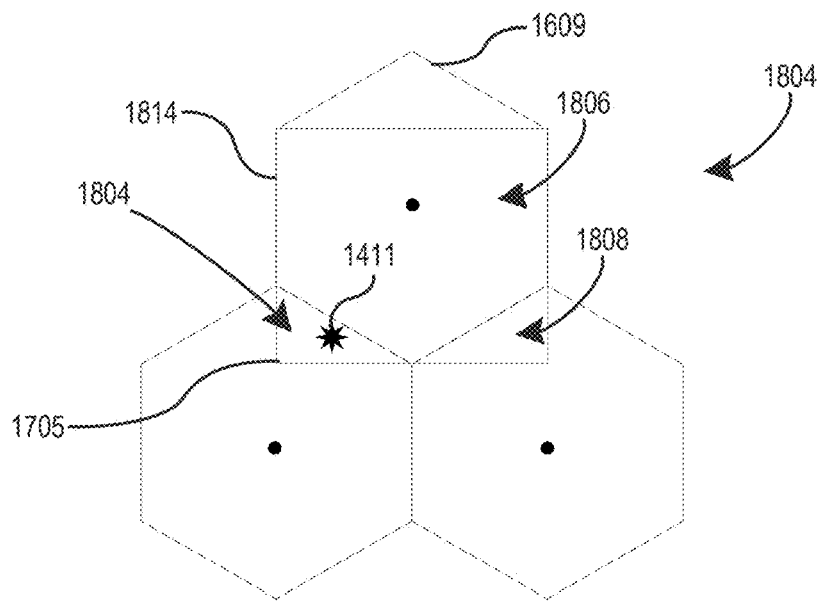
FIGS. 18A to 18C are schematic diagrams illustrating the associated regions of neighboring hexagonal tiles within a single rectangular tile, in accordance with one embodiment.
Figure 18B:
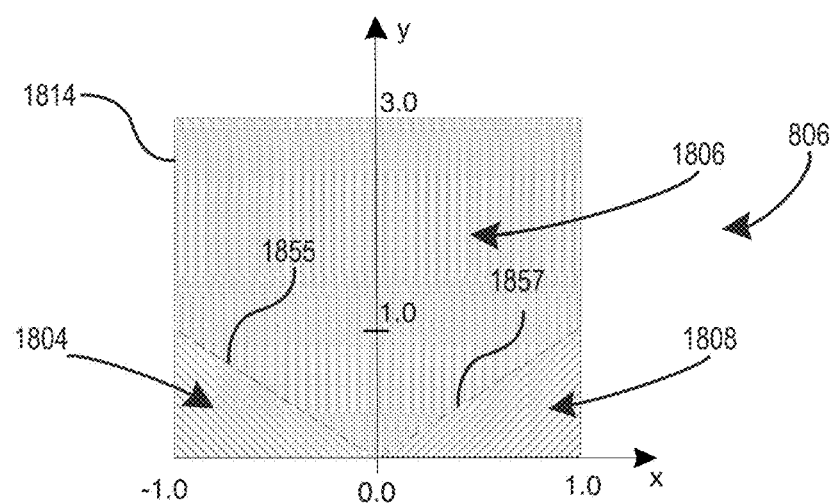
Figure 18C:
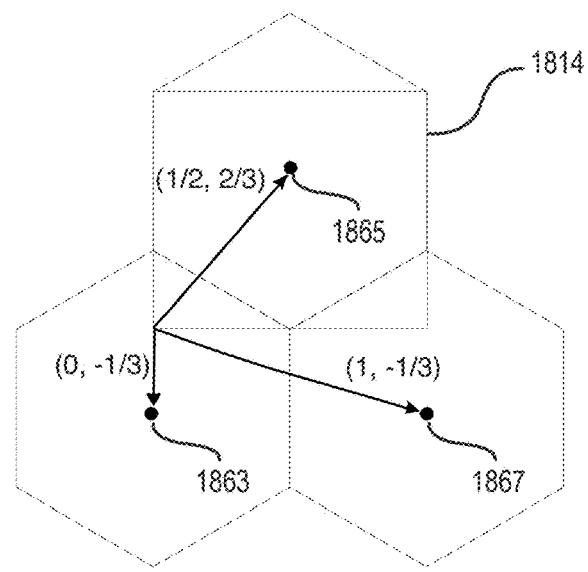

Once the position of lower left corner $\vec{C}_{corner}$ 1705 of the associated rectangular element 1814 containing the intersection point 1411 is known, three regions 1804, 1806 and 1807 within this rectangular element 1814 may be distinguished, as shown in FIGS. 18A to 18C. Each region is associated with a different hexagonal tile, as shown in FIG. 18A, namely, each region is delineated by the linear boundaries of adjacent underlying hexagonal tiles to define one region predominantly associated with a main hexagonal tile, and two opposed triangular tiles defined by adjacent hexagonal tiles on either side of this main tile. As will be appreciated by the skilled artisan, different hexagonal or nestled tile geometries will result in the delineation of different rectangular tile region shapes, as will different boundary profiles (straight vs. curved) will result in the definition of different boundary value statements, defined further below.

Continuing with the illustrated example, In step 1519, the coordinates within associated rectangular tile 1814 are again rescaled, as shown on the axis of FIG. 18B, so that the intersection point's location, within the associated rectangular tile, is now represented in the rescaled coordinates by a vector $\vec{d}$ where each of its x and y coordinates are given by:

$$d_x = 2*(uv_x - C_{corner_x}) - 1$$

$$d_y = 3*(uv_y - C_{corner_y})$$

Thus, the possible x and y values of the position of intersection point 1411 within associated rectangular tile 1609 are now contained within −1<x<1 and 0<y<3. This will make the next step easier to compute.

To efficiently find the region encompassing a given intersection point in these rescaled coordinates, the fact that, within the rectangular element 1814, each region is separated by a diagonal line is used. For example, this is illustrated in FIG. 18B, wherein the lower left region 1804 is separated from the middle "inverted house" region 1806 and lower right region 1808 by a downward diagonal line 1855, which in the rescaled coordinates of FIG. 18B, follows the simple equation y=−x. Thus, all points where x<−y are located in the lower left region. Similarly, the lower right region 1808 is separated from the other two regions by a diagonal line 1857 described by the equation y<x. Therefore, in step 1521, the associated region containing the intersection point is evaluated by using these two simple conditional statements. The resulting set of two Boolean values will thus be specific to the region where the intersection point is located. For example, the checks (caseL=x<y, caseR=y<x) will result in the values (caseL=true, caseR=false), (caseL=false, caseR=true) and (caseL=false, caseR=false) for intersection points located in the lower left region 1804, lower right region 1808 and middle region 1806, respectively. One may then convert these Boolean values to floating points values, wherein usually in most programming languages true/false Boolean values are converted into 1.0/0.0 floating point values. Thus, one obtains the set (caseL, caseR) of values of (1.0, 0.0), (0.0, 1.0) or (0.0, 0.0) for each of the described regions above.

To finally obtain the relative coordinates of the hexagonal center associated with the identified region, in step 1523, the set of converted Boolean values may be used as an input to a single floating point vectorial function operable to map each set of these values to a set of xy coordinates of the associated element center. For example, in the described embodiment and as shown in FIG. 18C, one obtains the relative position vectors of each hexagonal center $\vec{r}$ with the vectorial function:

$$\vec{r} = (r_x, r_y) = \left(0.5 + 0.5*(caseR - caseL), \frac{2}{3} - (caseR - caseL)\right)$$

thus, the inputs of (1.0, 0.0), (0.0, 1.0) or (0.0, 0.0) map to the positions (0.0, −⅓), (0.5, ⅔), and (1.0, −⅓), respectively, which corresponds to the shown hexagonal centers 1863, 1865 and 1867 shown in FIG. 8c, respectively, in the rescaled coordinates.

Now back to FIG. 15, we may proceed with the final step 1525 to translate the relative coordinates obtained above to absolute 3D coordinates with respect to the display or similar (i.e. in mm). First, the coordinates of the hexagonal tile center and the coordinates of the bottom left corner are added to get the position of the hexagonal tile center in the optical layer's frame of reference. As needed, the process may then scale back the values into absolute units (i.e. mm) and rotate the coordinates back to the original frame of reference with respect to the display to obtain the 3D positions (in mm) of the optical layer element's center with respect to the display's frame of reference, which is then fed into step 1116.

The skilled artisan will note that modifications to the above-described method may also be used. For example, the staggered grid shown in FIG. 17A may be translated higher by a value of ⅓ (in normalized units) so that within each rectangle the diagonals separating each region are located on the upper left and right corners instead. The same general principles described above still applies in this case, and the skilled technician will understand the minimal changes to the equations given above will be needed to proceed in such a fashion. Furthermore, as noted above, different LFSL element geometries can result in the delineation of different (normalized) rectangular tile regions, and thus, the formation of corresponding conditional boundary statements and resulting binary/Boolean region-identifying and center-locating coordinate systems/functions.

In yet other embodiments, wherein a rectangular and/or square microlens array is used instead of a nestled (hexagonal) array, a slightly different method may be used to identify the associated LFSL element (microlens) center (step 1114). Herein, the microlens array is represented by an array of rectangular and/or square tiles. The method, as previously described, goes through step 1515, where the x and y coordinates are rescaled (normalized) with respect to a microlens x and y dimension (henceforth giving each rectangular and/or square tile a width and height of 1 unit). However, at step 1517, the floor( ) function is used directly on each x and y coordinates of $\vec{uv}$ (the position vector of intersection point 1411) to find the coordinates of the bottom left corner associated with the corresponding square/rectangular tile. Therefrom, the relative coordinates of the tile center from the bottom left corner are added directly to obtain the final scaled position vector:

$$\vec{r}=(r_x,r_y)=(\text{floor}(uv_x)+0.5,\text{floor}(uv_y)+0.5)$$

Once this vector is known, the method goes directly to step 1525 where the coordinates are scaled back into absolute units (i.e. mm) and rotated back to the original frame of reference with respect to the display to obtain the 3D positions (in mm) of the optical layer element's center with respect to the display's frame of reference, which is then fed into step 1116.

The light field rendering methods described above (from FIGS. 11 to 20) may also be applied, in some embodiments, at a subpixel level in order to achieve an improved light field image resolution. Indeed, a single pixel on a color subpixelated display is typically made of several color primaries, typically three colored elements—ordered (on various displays) either as blue, green and red (BGR) or as red, green and blue (RGB). Some displays have more than three primaries such as the combination of red, green, blue and yellow (RGBY) or red, green, blue and white (RGBW), or even red, green, blue, yellow and cyan (RGBYC). Subpixel rendering operates by using the subpixels as approximately equal brightness pixels perceived by the luminance channel. This allows the subpixels to serve as sampled image reconstruction points as opposed to using the combined subpixels as part of a "true" pixel. For the light field rendering methods as described above, this means that the center position of a given pixel (e.g. pixel 1401 in FIG. 14) is replaced by the center positions of each of its subpixel elements. Therefore, the number of color samples to be extracted is multiplied by the number of subpixels per pixel in the digital display. The methods may then follow the same steps as described above and extract the associated image portions of each subpixel individually (sequentially or in parallel).

Figure 21A:
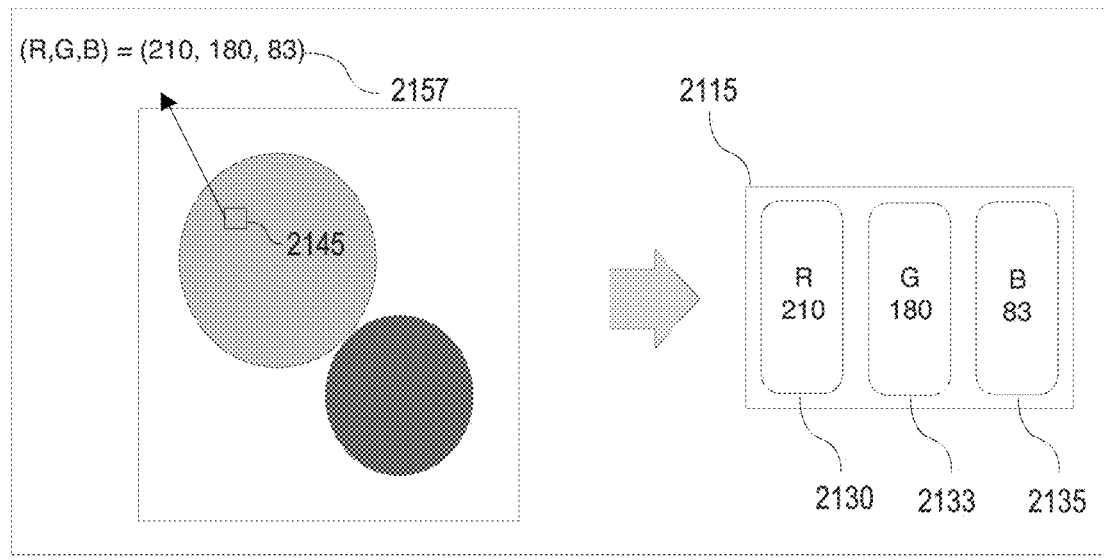
FIGS. 21A and 21B are schematic diagrams illustrating pixel and subpixel rendering, respectively, in accordance with some embodiments.
Figure 21B:
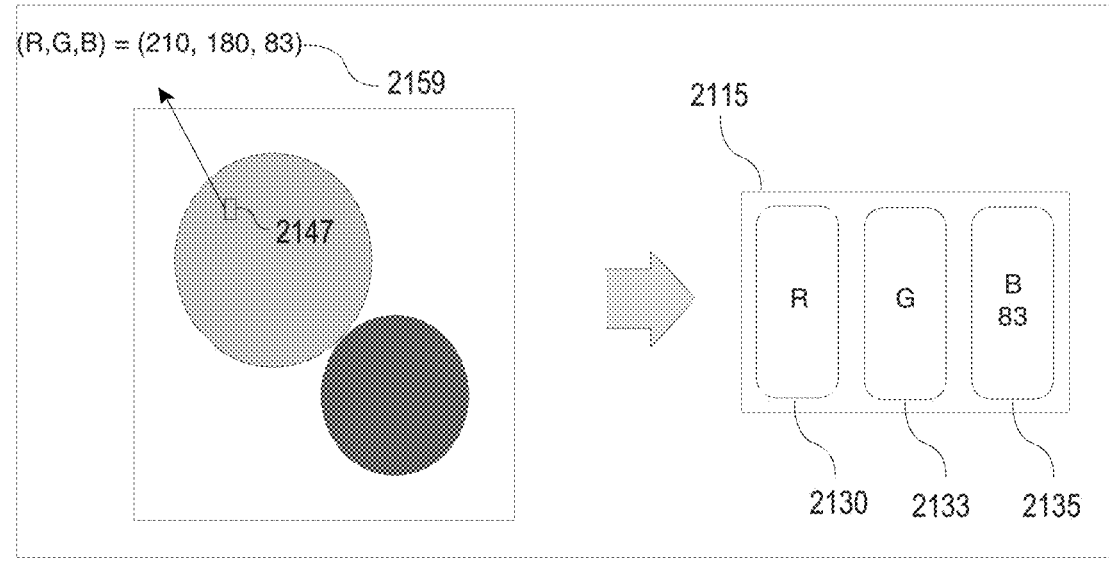

In FIG. 21A, an exemplary pixel 2115 is comprised of three RBG subpixels (2130 for red, 2133 for green and 2135 for blue). Other embodiments may deviate from this color partitioning, without limitation. When rendering per pixel, as described in FIG. 11 or in FIG. 19, the image portion 2145 associated with said pixel 2115 is sampled to extract the luminance value of each RGB color channels 2157, which are then all rendered by the pixel at the same time. In the case of subpixel rendering, as illustrated in FIG. 21B, the methods find the image portion 2145 associated with blue subpixel 2135. Therefore, only the subpixel channel intensity value of RGB color channels 2157 corresponding to the target subpixel 2135 is used when rendering (herein the blue subpixel color value, the other two values are discarded). In doing so, a higher adjusted image resolution may be achieved for instance, by adjusting adjusted image pixel colours on a subpixel basis, and also optionally discarding or reducing an impact of subpixels deemed not to intersect or to only marginally intersect with the user's pupil.

Figures 22A, 22B:
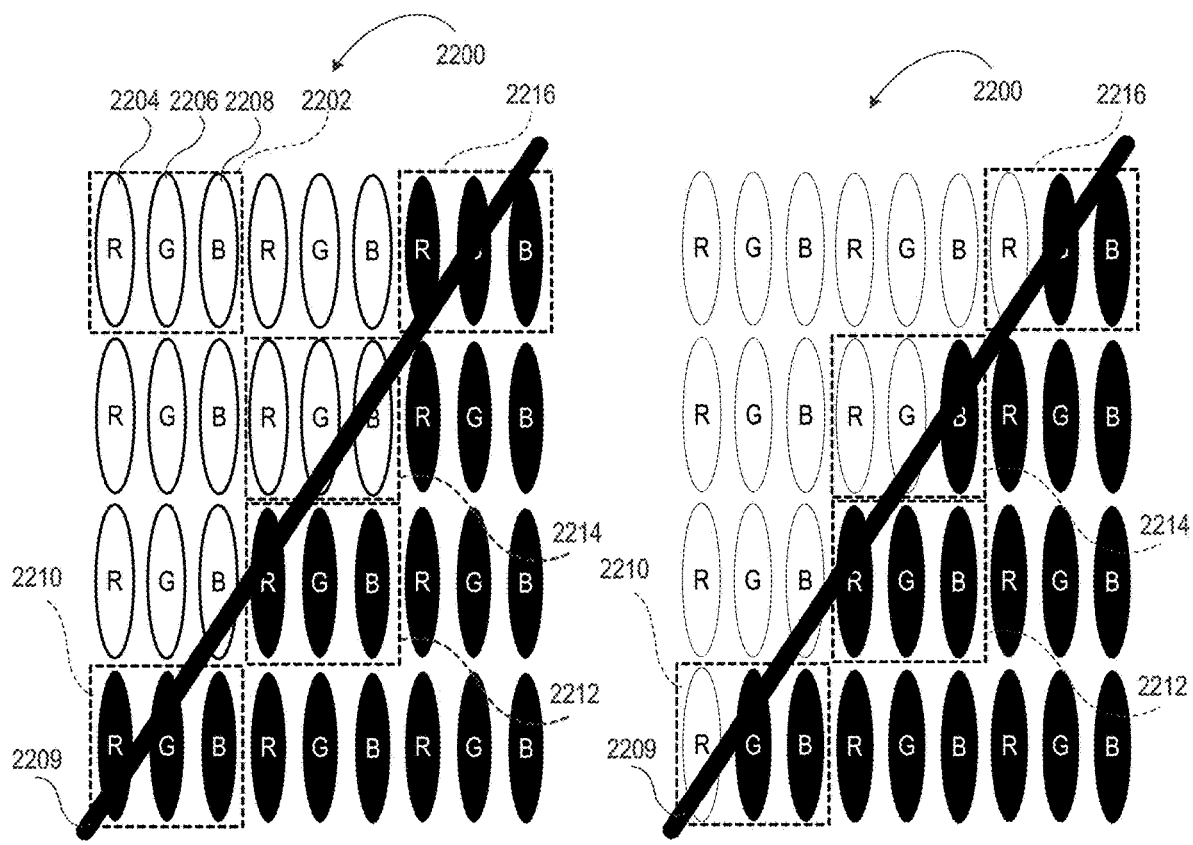
FIGS. 22A and 22B are schematic diagrams of an LCD pixel array defined by respective red (R), green (G) and blue (B) subpixels, and rendering an angular image edge using pixel and subpixel rendering, respectively, in accordance with one embodiment.

To further illustrate embodiments making use of subpixel rendering, with reference to FIGS. 22A and 22B, a (LCD) pixel array 2200 is schematically illustrated to be composed of an array of display pixels 2202 each comprising red (R) 2204, green (G) 2206, and blue (B) 2208 subpixels. As with the examples provided above, to produce a light field display, a light field shaping layer, such as a microlens array, is to be aligned to overlay these pixels such that a corresponding subset of these pixels can be used to predictably produce respective light field rays to be computed and adjusted in providing a corrected image. To do so, the light field ray ultimately produced by each pixel can be calculated knowing a location of the pixel (e.g. x,y coordinate on the screen), a location of a corresponding light field element through which light emanating from the pixel will travel to reach the user's eye(s), and optical characteristics of that light field element, for example. Based on those calculations, the image correction algorithm will compute which pixels to light and how, and output subpixel lighting parameters (e.g. R, G and B values) accordingly. As noted above, to reduce computation load, only those pixels producing rays that will interface with the user's eyes or pupils may be considered, for instance, using a complementary eye tracking engine and hardware, though other embodiments may nonetheless process all pixels to provide greater buffer zones and/or a better user experience.

In the example shown in FIG. 22A, an angular edge 2209 is being rendered that crosses the surfaces of affected pixels 2210, 2212, 2214 and 2216. Using standard pixel rendering, each affected pixel is either turned on or off, which to some extent dictates a relative smoothness of the angular edge 2209.

In the example shown in FIG. 22B, subpixel rendering is instead favoured, whereby the red subpixel in pixel 2210, the red and green subpixels in pixel 2214 and the red subpixel in pixel 2216 are deliberately set to zero (0) to produce a smoother representation of the angular edge 2209 at the expense of colour trueness along that edge, which will not be perceptible to the human eye given the scale at which these modifications are being applied. Accordingly, image correction can benefit from greater subpixel control while delivering sharper images.

In order to implement subpixel rendering in the context of light field image correction, in some embodiments, ray tracing calculations must be executed in respect of each subpixel, as opposed to in respect of each pixel as a whole, based on a location (x,y coordinates on the screen) of each subpixel. Beyond providing for greater rendering accuracy and sharpness, subpixel control and ray tracing computations may accommodate different subpixel configurations, for example, where subpixel mixing or overlap is invoked to increase a perceived resolution of a high resolution screen and/or where non-uniform subpixel arrangements are provided or relied upon in different digital display technologies.

Figure 23:
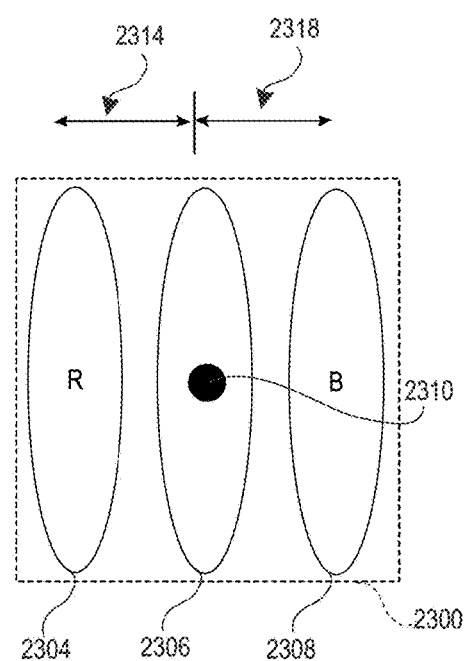
FIG. 23 is a schematic diagram of one of the pixels of FIG. 22A, showing measures for independently accounting for subpixels thereof apply subpixel rendering to the display of a corrected image through a light field display, in accordance with one embodiment.

In some embodiments, however, in order to avoid or reduce a computation load increase imparted by the distinct consideration of each subpixel, some computation efficiencies may be leveraged by taking into account the regular subpixel distribution from pixel to pixel, or in the context of subpixel sharing and/or overlap, for certain pixel groups, lines, columns, etc. With reference to FIG. 23, a given pixel 2300, much as those illustrated in FIGS. 22A and 22B, is shown to include horizontally distributed red (R) 2304, green (G) 2306, and blue (B) 2308 subpixels. Using standard pixel rendering and ray tracing, light emanating from this pixel can more or less be considered to emanate from a point located at the geometric center 2310 of the pixel 2300. To implement subpixel rendering, ray tracing could otherwise be calculated in triplicate by specifically addressing the geometric location of each subpixel. Knowing the distribution of subpixels within each pixel, however, calculations can be simplified by maintaining pixel-centered computations and applying appropriate offsets given known geometric subpixel offsets (i.e. negative horizontal offset 2314 for the red subpixel 12304, a zero offset for the green 2306 and a positive horizontal offset 2318 for the blue subpixel 2308). In doing so, light field image correction can still benefit from subpixel processing without significantly increased computation load.

While this example contemplates a linear (horizontal) subpixel distribution, other 2D distributions may also be considered without departing from the general scope and nature of the present disclosure. For example, for a given digital display screen and pixel and subpixel distribution, different subpixel mappings can be determined to define respective pixel subcoordinate systems that, when applied to standard pixel-centric ray tracing and image correction algorithms, can allow for subpixel processing and increase image correction resolution and sharpness without undue processing load increases.

In some embodiments, additional efficiencies may be leveraged on the GPU by storing the image data, for example image 1306, in the GPU's texture memory. Texture memory is cached on chip and in some situations is operable to provide higher effective bandwidth by reducing memory requests to off-chip DRAM. Specifically, texture caches are designed for graphics applications where memory access patterns exhibit a great deal of spatial locality, which is the case of the steps 1110-1126 of method 1100. For example, in method 1100, image 1306 may be stored inside the texture memory of the GPU, which then greatly improves the retrieval speed during step 1126 where the color channel associated with the portion of image 1306 at intersection point 1423 is determined.

Figure 24A:
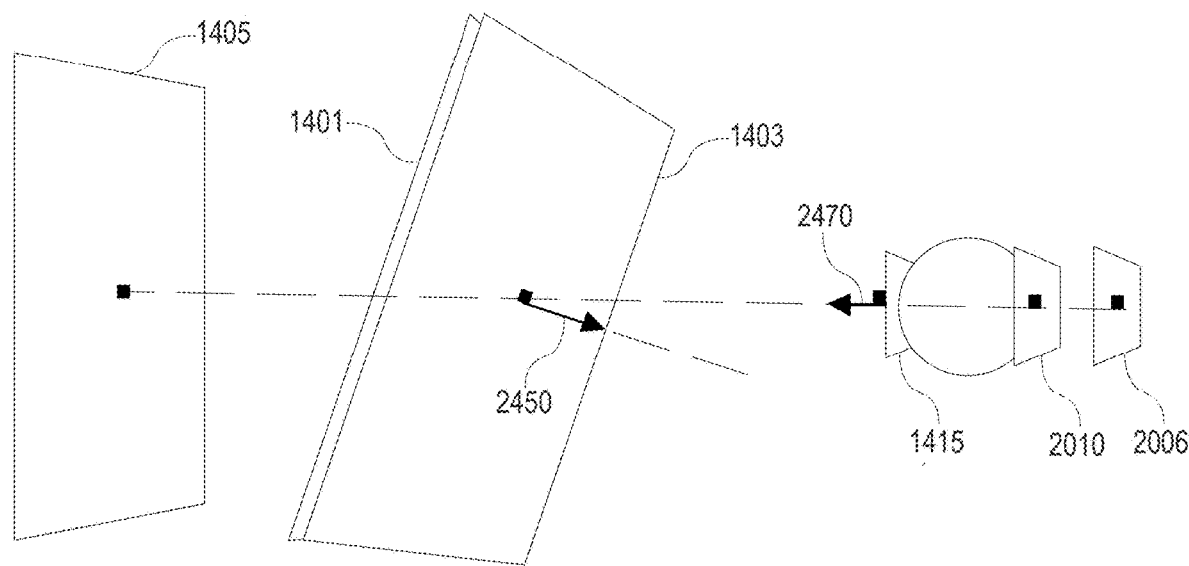
FIGS. 24A and 24B are schematic diagrams illustrating ray-tracing in the context of non-parallel planes, in accordance with one embodiment.
Figure 24B:
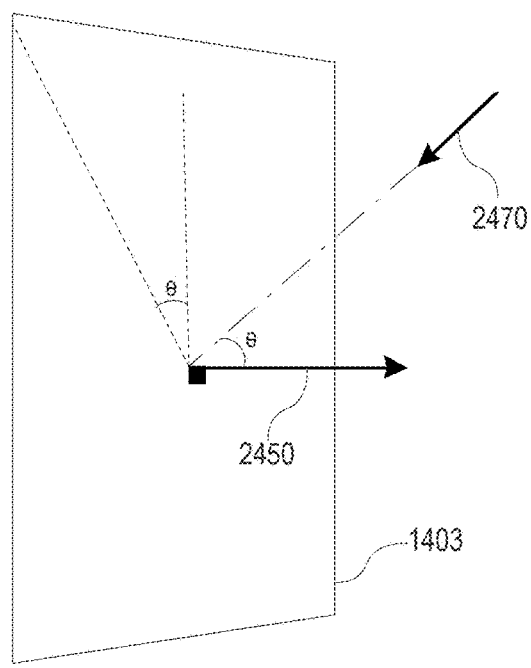

With reference to FIGS. 24A and 24B, and in accordance with one exemplary embodiment, ray-tracing with non-parallel planes will now be discussed. In FIGS. 14A to 14C and FIGS. 20A to 20D, the different planes illustrated (e.g. pixel display 1401, optical layer 1405, pupil plane 1415, virtual image plane 1405, retina plane 2010 and focus plane 2006) were all shown as being parallel to one another to better describe the ray-tracing methodology associated therewith. However, the corresponding ray-tracing methods 1100 of FIG. 11 and 1900 of FIG. 19, as described above, may also be applied to account for changes in the relative orientation between any one of those planes.

In some embodiments, and as illustrated in FIG. 24A, cases may be considered wherein the user is viewing the light field display at an angle. In this specific example, the ray-tracing method can therefore account for a change in orientation of the pupil plane 1415 with respect to the pixel display 1401 and optical layer 1405. In this example, other planes such as virtual image plane 1405 (used in the ray-tracing method of FIG. 11), and retina plane 2010 and focus plane 2006 (used in the ray-tracing method of FIG. 19) may be taken to be parallel to pupil plane 1415. The relative difference in orientation between the two sets of planes is illustrated by using vector 2450 which is the normal vector to the plane of corresponding optical layer 1403, and vector 2470 which is the normal vector to pupil plane 1415. The relative orientation between the two normal vectors is illustrated in FIG. 24B, using polar and azimuthal angles.

The general orientation of pupil plane 1415 may be parametrize, for example, by using the 3D location of pupil center 1417 and a corresponding normal vector. Such a normal vector may be taken to be, in some embodiments, equal to the gaze direction as measured by a gaze tracking system or similar, as will be discussed below.

Once the relative position and orientation of pupil plane 1415 is determined, the relative position/orientation of all remaining planes (parallel or non-parallel) may be determined and parametrized accordingly. Planes that are parallel share the same normal vector. From there, the methods of FIGS. 11 and 19 can be applied by finding the intersection point between an arbitrary vector and an arbitrarily oriented plane, as is done for example at steps 1112, 1118, 1124 of the method of FIG. 11, and steps 1912, 1918, 1923, 1925 of the method of FIG. 19.

In the illustrated example of FIG. 24A, the position of virtual image plane 1405 may be computed using the minimum reading distance 1310 (and/or related parameters) but from the position of pupil plane 1415 and along the direction vector 2470.

To extract normal vector 2470 of pupil plane 1415, the eye tracking methods and systems described above may be used or modified to further provide a measure of the eye's gaze direction (e.g. gaze tracking). As discussed above, there are many known eye tracking methods in the art, some of which may also be used for gaze-tracking. For example, this includes Near-IR glint reflection methods and systems or methods purely based on machine vision methods. Hence, in some embodiments, pupil plane 1415 may be re-parametrize using an updated 3D location of pupil center 1417 and an updated normal vector 2470 at each eye tracking cycle. In other embodiments, a hybrid gaze tracking/pupil tracking system or method may be used wherein gaze direction (e.g. normal vector 2470) is provided at a different interval than pupil center location 1417. For example, in some embodiments, for one or more cycles, only the 3D pupil center location 1417 may be measured and an old gaze direction vector may be re-used or manually updated. In some embodiments, an eye model or similar may be constructed to map a change in measured pupil center location 1417 to a change in the gaze direction vector without relying on the full capabilities of the gaze tracking system or method. Such a map may be based on one or more previous gaze tracking measurements. In any case, by measuring/determining the 3D pupil center location 1417 and normal vector 2470, the pupil plane may be parametrized accordingly.

Note that in FIG. 24A, display 1401 and optical layer 1403 are shown parallel for simplicity, but other embodiments may envision optical layer 1403 to be non-parallel to display 1401 as well. This doesn't change the general scope of the present discussion, as long as the relative angle between them is known. For example, such an angle may be pre-determined during manufacturing or measured in real-time using one or more sensors (for example in the case where optical layer 1403 may be mobile). Similarly, other planes like for example retina plane 2010 may also be made to be non-parallel to the pupil plane, depending on the user's eye geometry.

Figure 25:
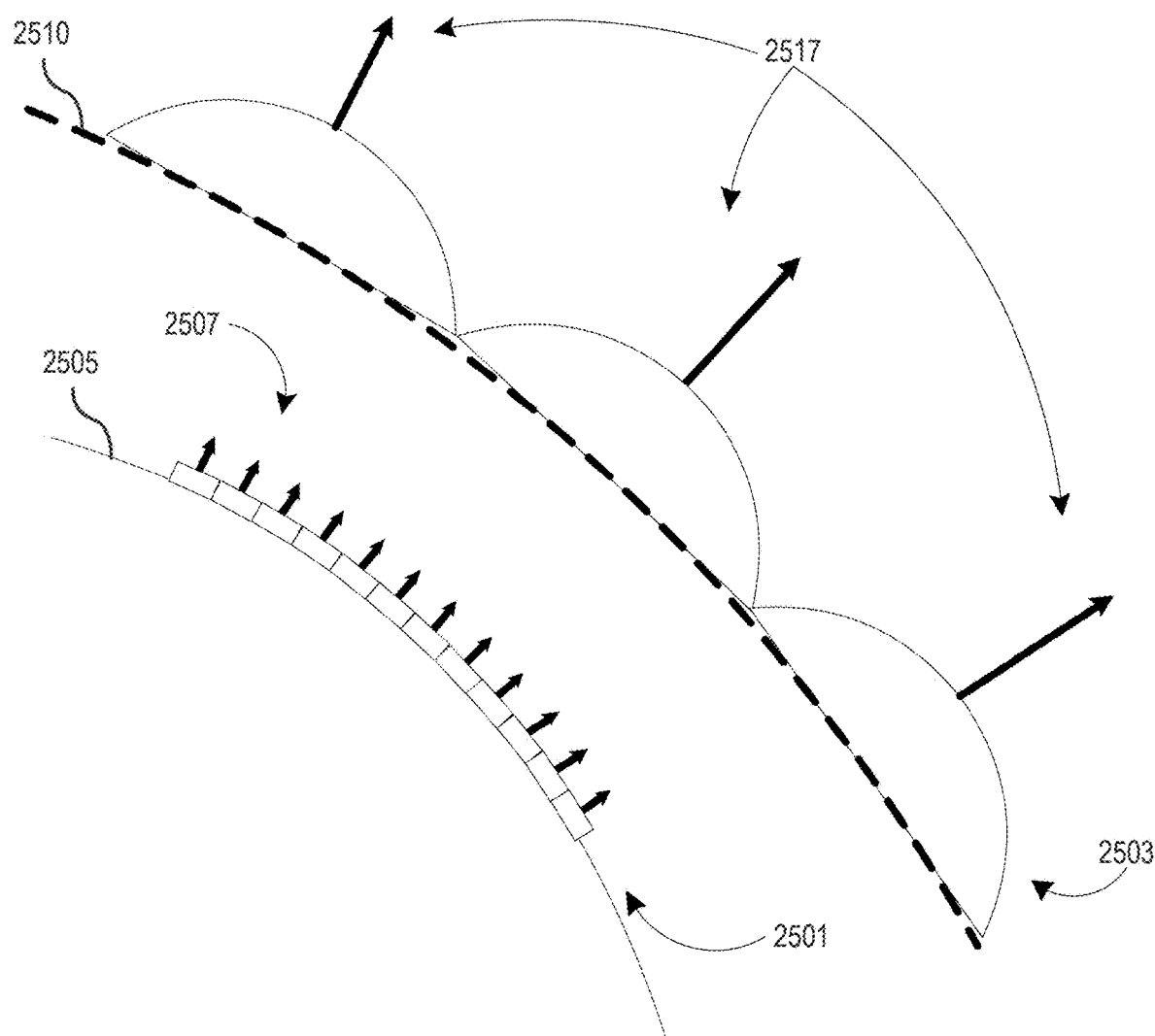
FIG. 25 is a schematic diagram illustrating ray-tracing in the context of curved surfaces such as a curved pixel display and curved light field shaping layer, in accordance with one embodiment.

In some embodiments, one or more planes discussed above may be replaced with non-planar surfaces. For example, a curved light-field display may be used. In one non-limiting example, a curved pixel display 2501 and optical layer 2503 may be considered, as is shown in FIG. 25. In this Figure, each element of pixel display 2501 follows a curve 2505. Similarly, each optical element of optical layer 2503 is located along another curve 2510. Such curved surfaces may be parametrized by defining a parametrized normal vector at each point of interest (e.g. pixel center location and/or optical element center). Thus, in this example, a set of normal vectors 2507 and a set of normal vectors 2517 are illustrated for each pixel and each light field shaping element, respectively. An example of curve pixel displays may include flexible OLED displays, thought other flexible display technologies may be considered, as can different light field shaping element array configurations and technologies be contemplated. As long as the curve parameters are known, the normal surface vector at any point (e.g. pixel and/or lenslet) may also be computed. For example, the curve parameters may be set during manufacturing or be measured by one or more sensors. Thus, the ray-tracing methods of FIGS. 11 and 19 may be used as described, with the change that each (pixel/subpixel and/or light shaping element) will have its normal vector. Intersection between rays and these curved surfaces proceeds therefore as described above.

With reference to FIGS. 26 to 31, and in accordance with one exemplary embodiment, a compressive light field rendering method will now be discussed. Compressive light field rendering consists of considering the complete image generated from all pixels/subpixels in pixel display 1401 so as to find the optimized combination of such pixel/subpixel values that most efficiently generate the image. This may result in fewer display pixels being necessary to emit a given light field than a direct optical solution would require, like methods 1100 and 1900 for example. Indeed, in raytracing methods 1100 and 1900 of FIGS. 11 and 19, the value of each pixel/subpixel is set subsequently. In contrast, in a compressive light field approach, the entire set of pixel/subpixel values generating a best or optimized image is derived at the same time. This approach further considers that a light beam (and not a single ray vector) is emitted by each pixel/subpixel, and that this beam may overlap multiple points on the image generated. Thus, by evaluating the full rendered image for a given set of pixel/subpixel values, a cost function or similar may be constructed which quantifies the difference between the input image 1306 (FIG. 13) to be displayed and the actual image being generated by the current set of all pixel/subpixel values. By minimizing this difference, the best or optimized set of values of all pixels/subpixels may be found.

As an example, let x be the set of all pixel/subpixel values (e.g. sampled color/channel), and y be the set of corresponding values of image portions of image 1306. A transport or transfer function A may be constructed to simulate how the light emitted from an input set of values x generates the set of image values y (e.g. how a given set of x maps to a given set of y). This may be represented as the following system:

$$A \cdot x = y.$$

Figure 26:
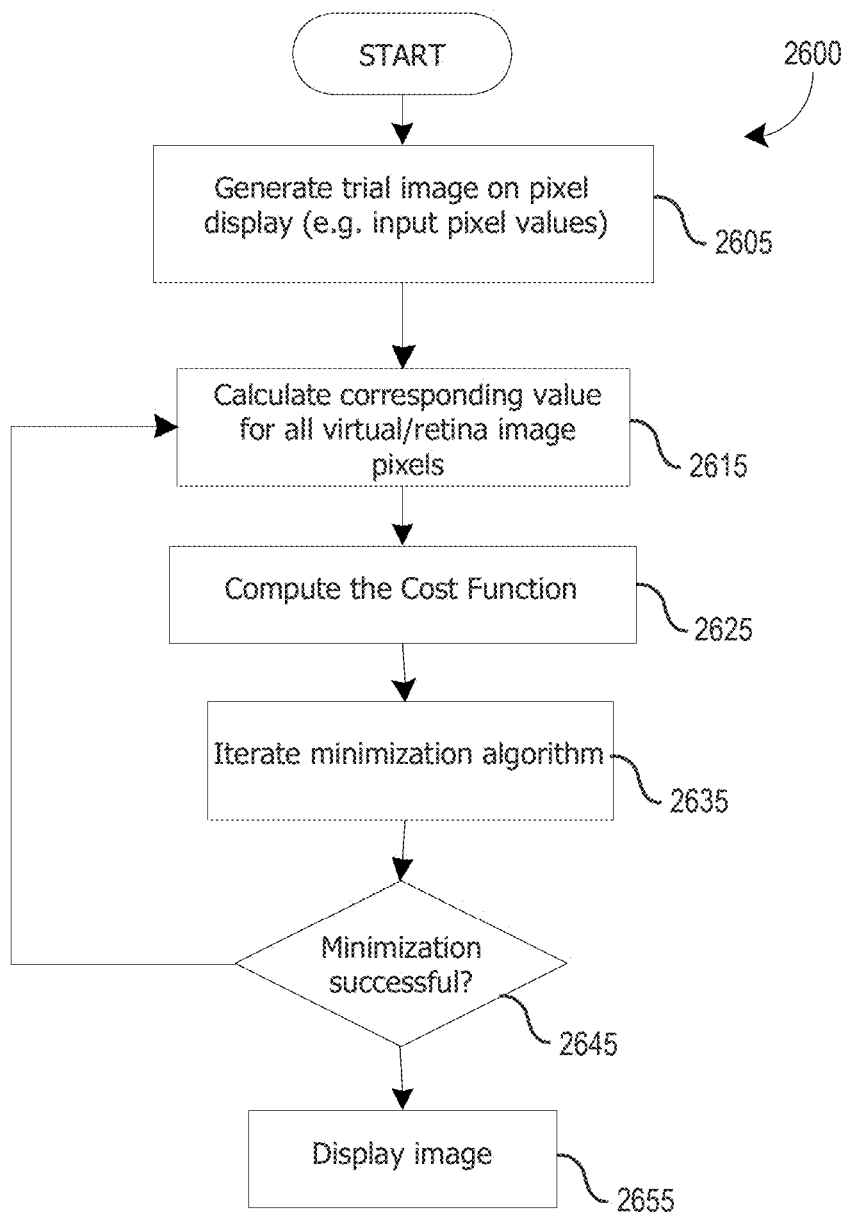
FIG. 26 is a process flow diagram of an illustrative compressive light field rendering process, in accordance with one embodiment.

In some embodiments, the currently described compressive lightfield rendering method is operable to find the best set of values x that generate the set of values y that are the closest to the digitized input image 1306 (e.g. $y^{image}$) The procedure to do so, in accordance with one embodiment, is illustrated as process 2600 in FIG. 26, which illustrates a single light field rendering iteration.

At step 2605, an initial or guess input set of values x is used to start the rendering iteration. In general, this initial set of values may be anything but in practice, the closer the initial set of values x is to the solution, the faster finding the solution will be. Thus, in some embodiments, the input image 1306 may be used (e.g. $x = y^{image}$), or in other embodiments a single iteration of the ray tracing method 1100 may be used instead.

Figure 27:
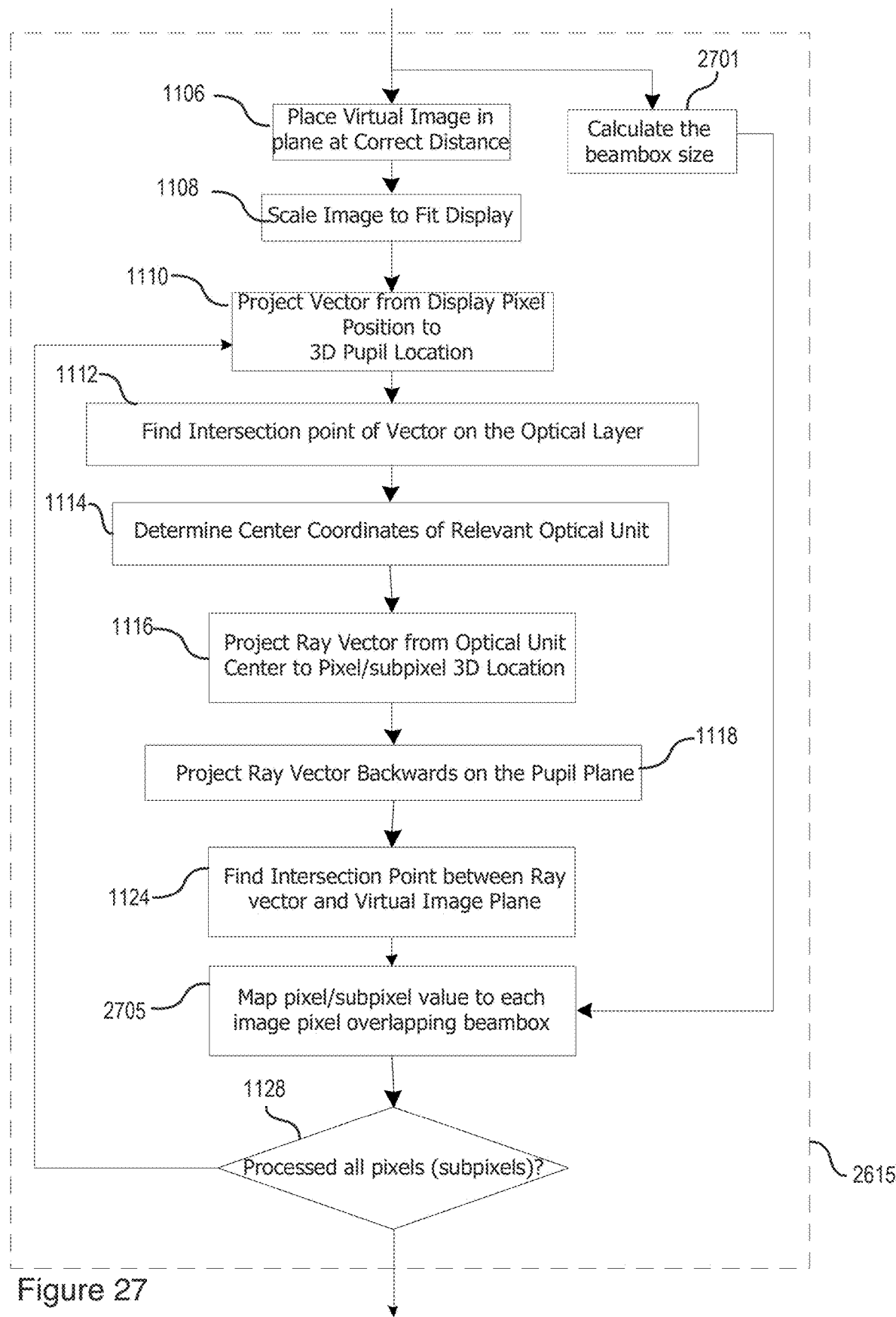
FIG. 27 is a process flow diagram of an illustrative ray tracing process for the compressive light field rendering process of FIG. 26 when optionally implemented within the context of the process of FIG. 11, in accordance with one embodiment.
Figure 31:
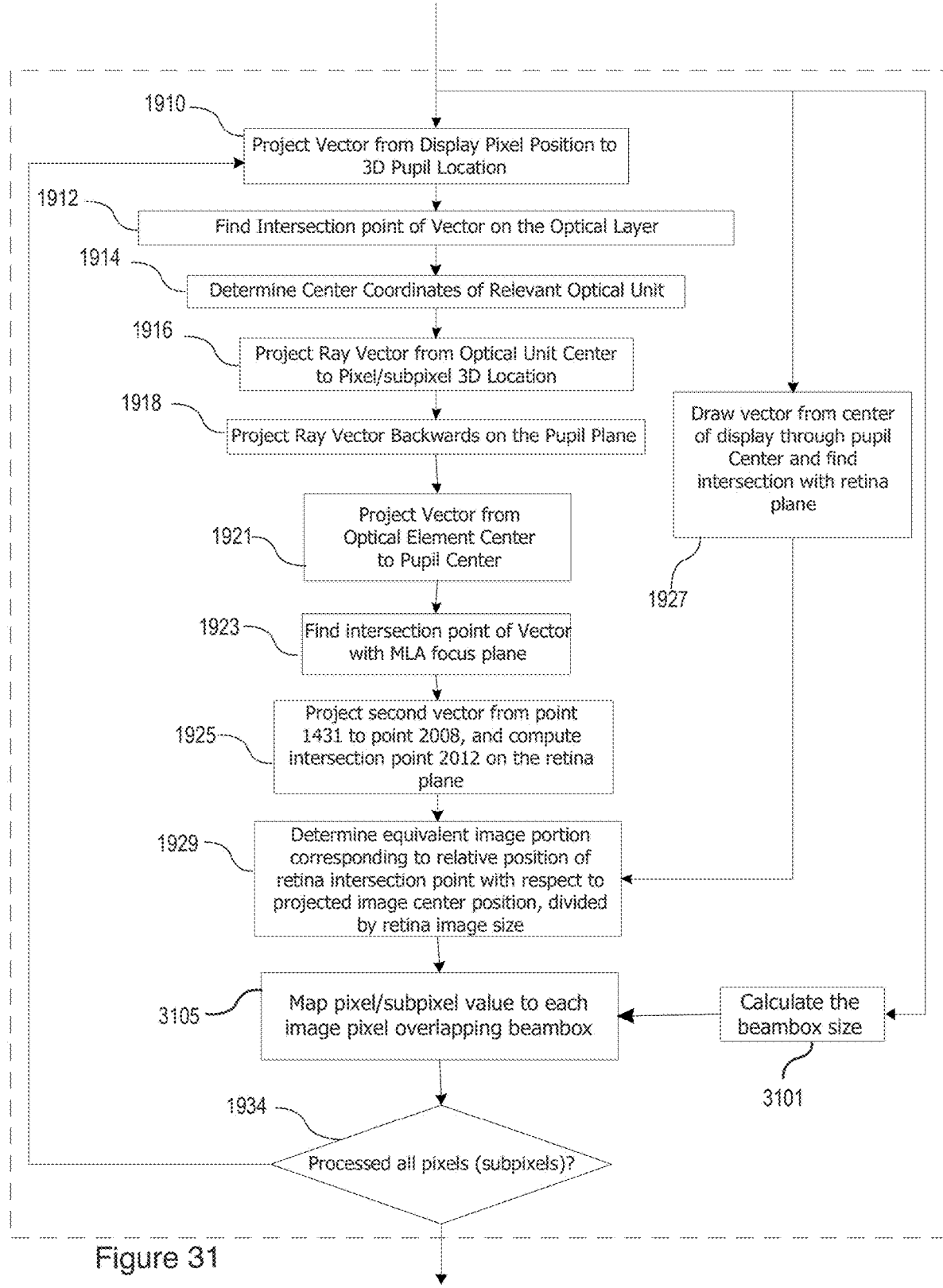
FIG. 31 is a process flow diagram illustrating an exemplary ray tracing process for the compressive light field rendering process of FIG. 26 when optionally implemented within the context of the process of FIG. 11, in accordance with another embodiment.

At step 2615, the current set of pixel/subpixel values x is used to generate the corresponding pixelated image values y. As mentioned above, this is done by modelling how a light beam from each pixel/subpixel is projected on the perceived image. FIGS. 27 and 31 illustrate how the beam mapping is calculated, in some embodiments, by using a modified version of the ray tracing methods 1100 or 1900, respectively.

As mentioned above, the beam of light emitted by a single pixel/subpixel may overlap multiple image portions. To determine how a given beam overlaps the image, a modified ray tracing method may be used, wherein the width of the beam is considered. To quantify which image portion the beam overlaps, it is useful to consider a digitized or pixelated image, either on the virtual plane or on the retina plane. For example, by defining an image resolution (which may or may not be the same as the pixel display resolution), the image size may be divided by this image resolution to define image pixels, each having a precise boundary on the relevant plane. By determining which of these (image pixels) overlaps with the beam, the value of the relevant pixel/subpixel may be added to this (image pixel). By adding the contribution of all pixel/subpixels to all (image pixel), the full set of values y may be determined. Furthermore, as will be explained below, these image pixels may either be on virtual image plane 1405—wherein they may be referred to as virtual pixels—or as projected on retina plane 2010—wherein they may be referred to as retina pixels).

Two methods of tracing the beam will now be explained, one based on a modified version of ray tracing method 1100 described in FIG. 11, the other based on a modified version of ray tracing method 1900 described in FIG. 19.

With reference to FIG. 27, and in accordance with one exemplary embodiment, a modified ray tracing method based on ray tracing method 1100 of FIG. 11 will now be discussed. In general, the ray tracing method is used to find the intersection point 1423 of the center of the beam with the virtual plane. Thus, steps 1106, 1108, 1110-1118, 1124 and 1128 proceed exactly as described above. However, the beam of light emitted by a pixel/subpixel will also cover an area (herein referred to as the beambox) centered around intersection point 1423. Thus, a new step 2701 is added wherein the size of the beambox on virtual plane 1405 is calculated.

Figure 28:
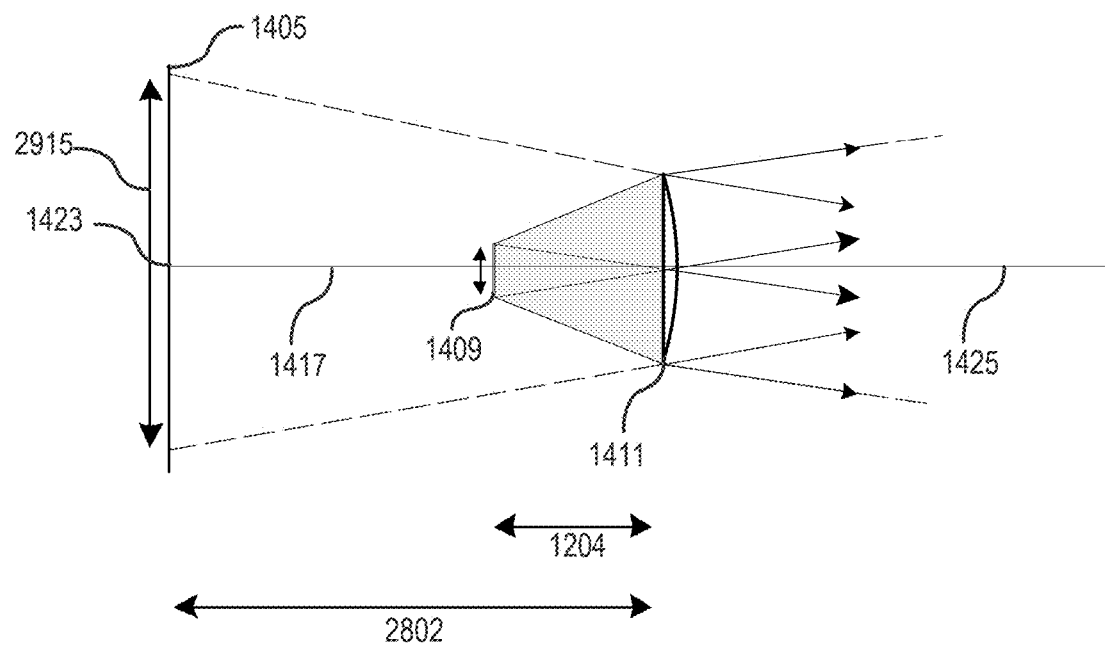
FIGS. 28 and 29 are schematic diagrams illustrating certain process steps of FIG. 27.
Figure 29:
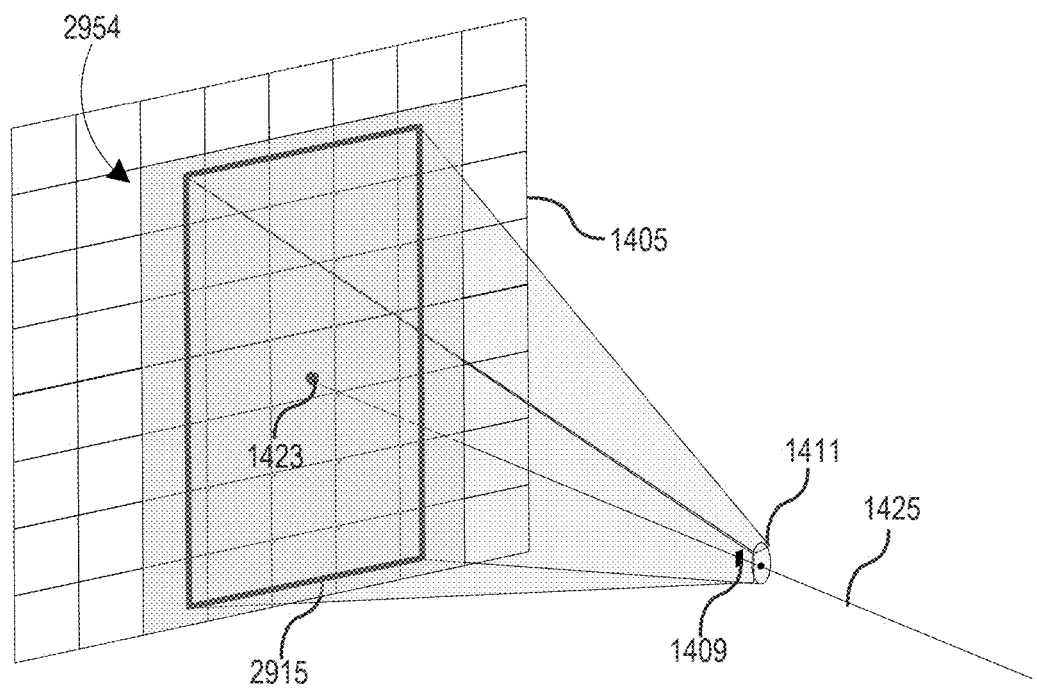

In some embodiments, as illustrated in FIG. 28, the shape and size of the beam box on virtual plane 1405 may be estimated by computing the propagation of the light beam backwards from the optical layer 1411. In the exemplary geometry considered in FIG. 28, this leads to a rectangular beambox 2915 centered on intersection point 1423, the dimensions of which may be directly calculated by scaling the size of the source pixel/subpixel, resulting in a rectangular beambox 2915 on the virtual image plane 1405. In this example, the size of the beambox 2915 in one dimension may be found by multiplying the size of the pixel/subpixel 2905 by the ratio of the distance between the optical layer 1411 to the virtual plane 1405 to the distance between the pixel/subpixel to the optical layer 1204.

Note that while the size of each virtual pixel depends on the position of the virtual image plane (which dictates the scaling necessary so that the image fills out the display as perceived by the user), the size of the beam box is also a function of constant parameters 1102. Since the size of the beambox is fixed for a given light field rendering iteration, step 2701 may be done once, for example before step 2615 in FIG. 26. The skilled artisan will understand that other ways of calculating the width of the beam on the virtual plane may be used, for example by using geometric or diffractive optics.

Figure 30:
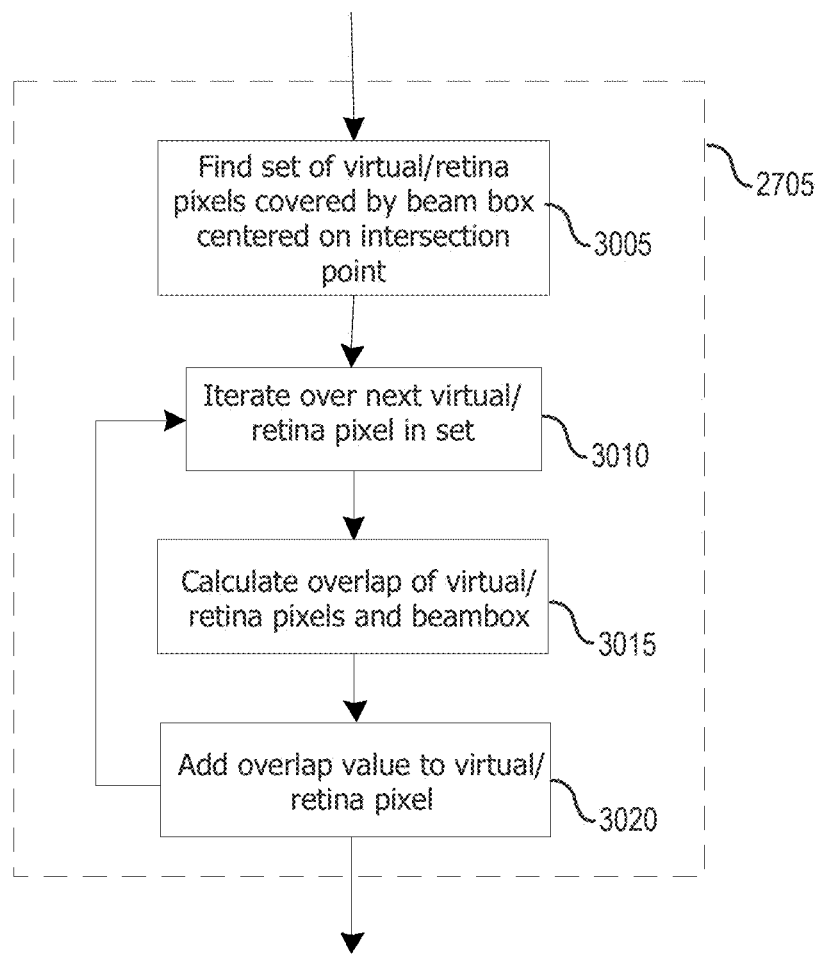
FIG. 30 is a process flow diagram illustrating an beam overlap calculation of the process of FIG. 27, in accordance with one embodiment.

Once the position of the intersection point 1423 on image 1306 is found at step 1124, at step 2705, the contribution of the pixel/subpixel corresponding to the beambox is added to each virtual pixel at least partly inside the beambox. An exemplary implementation of step 2705 is shown in FIG. 30. At step 3005, the list of every virtual pixel overlapping, at least partly, the beambox is found. Therefrom, at step 3010, the method may iterate over each of these virtual pixels. At step 3015, the area overlap between the virtual pixel and the beambox is computed (e.g. the proportion of the beambox area covered by this virtual pixel). This is also illustrated schematically in FIG. 29, which shows an example of the set of all virtual pixels 2954 overlapping beambox 2915 centered on intersection point 1423 for a given rectangular configuration. It is clear that some virtual pixels receive more light from the source pixel/subpixel 1409 than others and this overlap factor takes that into account. Furthermore, in some embodiments, the overlap factor may also consider the relative radiant flux one virtual pixel receives from the pixel/subpixel 1409. Once the overlap factor has been calculated for a given virtual pixel, going back to step 3020, the value of pixel/subpixel 1409 is multiplied by the overlap factor before being added to the current value of the virtual pixel. In some embodiments, the pixel/subpixel value may be further multiplied by a pupil transmission factor which estimates what amount of the light beam makes it through the pupil, wherein this transmission factor is zero if the light from the beam is estimated to not reach the pupil at all.

In some embodiments, the set of values y may instead represent the actual image being generated on the user's retina (e.g. on retina plane 2010 instead of on virtual plane 1401). Thus, in some embodiments, step 2615 may instead be based on a modified version of the ray tracing method 1900 of FIG. 19. This is illustrated in FIG. 31, in which the illustrated steps 1910 to 1929 proceed as described in the ray-tracing method of FIG. 19 (e.g. to find the intersection point 2012 on the retina plane, onto which the beambox will be centered), and steps 3101 and 3105 mirror steps 2701 and 2705 described above with reference to FIG. 27 (including exemplary steps 3005 to 3020 of FIG. 30), with the difference being that the beambox size is calculated on retina plane 2010 and not on virtual image plane 1405. The size of the beambox on the retina plane may be derived similarly as discussed above, however taking into account the effect of the eye lens. Moreover, the size of a retina pixel (e.g. image portion on the retina plane) used to calculate the overlap factor in step 3105 may be computed using the retina image size 2031 which was computed at step 1929 and dividing by the retina image resolution.

Furthermore, the skilled artisan will understand that step 2615 as described in either FIG. 27 or in FIG. 31 may also equally be applied in the case of non-parallel planes, as already discussed (e.g. ray-tracing in the context of curved surfaces).

Going back to FIG. 26, once the set of values A·x=y has been determined, at step 2625, the value of the cost function (CF), which quantifies the difference between the pixel/subpixel values of pixel display 1401 and the corresponding image portion (e.g. virtual/retina pixel) of the light field corrected image is computed. In the current example, a quadratic error function was considered:

$$CF = \Sigma (A(x_i) - y_i^{image})^2$$

wherein $x_i$ is the (value) of pixel/subpixel i and $y_i^{image}$ is the corresponding virtual/retina pixel/subpixel value of input image 1306. However, the skilled technician will understand that different types of error functions may be used instead. For example, these may include, without restriction, absolute or mean absolute error functions, a Huber loss function, a log-cos h function, etc. Note that, in some embodiments, the chosen optimization algorithm may also require the gradient or the Hessian of the cost function. This may be computed at this step as well. The derivatives and/or Hessian values may be given in an analytical form, or be computed numerically.

As mentioned above, the optimized values of each pixel/subpixel of pixel display 1401 may be determined by minimizing the cost function described above using a numerical algorithm for solving unconstrained nonlinear optimization problems. Some examples of such algorithms include, without limitation, gradient/steepest descent, conjugate gradient, or iterative Quasi-Newton methods such as the limited-memory Broyden-Fletcher-Goldfarb-Shanno (L-BFGS or LM-BFGS) algorithm or similar. These algorithms are generally iterative, wherein the value of x is changed incrementally in a direction that reduces the value of the error function. Thus, at step 2635, a minimization step is taken to obtain a new set of values x (e.g. new values for all pixels/subpixels).

At step 2645, the convergence of the minimization procedure is evaluated. In the case where it has indeed converged (e.g. the cost function has been minimized), the last set of values x is taken to be the finalized pixel display configuration and the light field image is rendered on pixel display 1401 at step 2655. If the minimization algorithm hasn't converged at this point, steps 2615 to 2635 are repeated until it does, or until a maximum number of iteration steps has been reached. The skilled technician will understand that different convergence criteria may be used. Similarly, the maximum number of minimization steps may be changed, depending on the constraints upon the rendering speed for example.

Unrestricted, the minimization procedure discussed above may produce values that are outside of the displayable range (e.g. outside of the range [0,1]). Thus, in some embodiments, the cost function may be modified so as to improve the probability that the minimization procedure results in values within the displayable range. For example, in some embodiments, a factor of $(x-½)^2$ or $abs|x-½|$ may be added to the cost function, for the range of values outside of [0, 1]. In some embodiments, a constant value of 0.25 may also be added for values inside this range.

Furthermore, method 2600 in general may, in some embodiments, be implemented to work on massively parallel processing devices, for example on a GPU or similar, as was discussed above.

The methods and systems described above were mainly discussed in the context of correcting vision problems such as nearsightedness, farsightedness and astigmatism. However, these methods and systems may equally be used to provide vision correction for higher order aberrations. Generally, it is common to describe higher order aberrations mathematically using so-called Zernike polynomials, which describe how the light wave front entering the eye is distorted by the aberration. For example, higher order aberrations such as spherical aberrations, coma, and trefoil may be represented by a second order Zernike polynomial function. In some embodiments, the light field rendering methods and systems described above may be used to generate a light field that compensates for such higher order aberrations. In some embodiments, this may include generating a curved or distorted image plane based on or derived from, in some instances, the corresponding Zernike polynomial function. Moreover, methods for generating a vision corrected light field image with curved surfaces were already described above. Thus, in some embodiments, the rendering methods 1100, 1900, or 2600 may be equally applied, but with the added characteristic that, for example, the virtual image is curved or distorted.

While the present disclosure describes various exemplary embodiments, the disclosure is not so limited. To the contrary, the disclosure is intended to cover various modifications and equivalent arrangements included within the general scope of the present disclosure.

What is claimed is:

1. A computer-implemented method, automatically implemented by one or more digital processors, to automatically adjust perception of an input image to be rendered via a set of pixels and a corresponding array of light field shaping elements (LFSE), the method comprising:

computing an adjusted image on an adjusted image plane corresponding to a set of display pixel values, said adjusted image being defined as a set of adjusted image pixel values corresponding to a set of image pixels or portions, and wherein:

for a trial set of display pixel values derived from said input image:

for at least some of said pixels, digitally:

projecting an adjusted image ray trace between said given pixel and a given LFSE to intersect said adjusted image plane at a given adjusted image location, given an estimated direction of a light field emanated by said given pixel given said given LFSE;

calculating a beam box region on said adjusted image plane centered on said adjusted image location characterizing the area illuminated by said given pixel;

identifying one or more image pixels overlapping with said beam box region, and;

for each of said overlapping image pixels:

adding to said image pixel value a pixel value of said display pixel;

calculating a cost function value between said adjusted image and said trial input image, said cost function value quantitatively characterizing a difference between said set of image pixel values and said input image;

deriving a new set of display pixel values reducing said cost function value;

repeating said computing an adjusted image, said calculating a cost function value and said deriving a new set of display pixel values, each time using said new set of display pixel values, until said difference parameter has been minimized; and rendering for each pixel in said set of pixels the corresponding pixel value from said set of display pixel values corresponding to said minimized difference parameter, thereby rendering a perceptively adjusted version of the input image.

2. The method of claim 1, wherein said pixel value is multiplied by a ratio of overlap between said overlapping image pixel and said beam box before being added to said image pixel value.

3. The method of claim 1, wherein said pixel value is multiplied by a relative radiant flux factor.

4. The method of claim 1, wherein said pixel value is multiplied by a pupil transmission factor characterizing how much light from said ray reaches the user's pupil.

5. The method of claim 1, wherein said adjusted image plane is a virtual image plane virtually positioned relative to the digital display at a designated distance from said user pupil location, and wherein said adjusted image ray trace comprises a virtual image vector between said given pixel and said given LFSE to intersect said virtual image plane.

6. The method of claim 1, wherein said adjusted image plane is designated as a user retinal plane, and wherein said adjusted image ray trace is projected to intersect with said user retinal plane by redirecting said adjusted image ray trace given said pupil location in accordance with an input user eye focus aberration parameter.

7. The method of claim 1, wherein said user pupil location is dynamically tracked via a pupil or eye tracker.

8. The method of claim 1, wherein the user perception is adjusted so to at least partially address the user's reduced visual acuity.

9. A non-transitory computer-readable medium comprising digital instructions to be implemented by one or more digital processors to automatically adjust user perception of an input image to be rendered via a set of pixels and a corresponding array of light field shaping elements (LFSE), by:

computing an adjusted image on an adjusted image plane corresponding to a set of display pixel values, said adjusted image being defined as a set of adjusted image pixel values corresponding to a set of image pixels or portions, and wherein:

for a trial set of display pixel values derived from said input image:

for at least some of said pixels, digitally:

projecting an adjusted image ray trace between said given pixel and a given LFSE to intersect said adjusted image plane at a given adjusted image location, given an estimated direction of a light field emanated by said given pixel given said given LFSE;

calculating a beam box region on said adjusted image plane centered on said adjusted image location characterizing the area illuminated by said given pixel;

identifying one or more image pixels overlapping with said beam box region, and;

for each of said overlapping image pixels:

adding to said image pixel value a pixel value of said display pixel;

calculating a cost function value between said adjusted image and said trial input image, said cost function value quantitatively characterizing the difference between said set of image pixel values and said input image;

deriving a new set of display pixel values reducing said cost function value;

repeating said computing an adjusted image, said calculating a cost function value and said deriving a new set of display pixel values, each time using said new set of display pixel values, until said difference parameter has been minimized; and rendering for each pixel in said set of pixels the corresponding pixel value from said set of display pixel values corresponding to said minimized difference parameter, thereby rendering a perceptively adjusted version of the input image.

10. The non-transitory computer-readable medium of claim 9, wherein said pixel value is multiplied by a ratio of overlap between said overlapping image pixel and said beam box before being added to said image pixel value.

11. The non-transitory computer-readable medium of claim 9, wherein said pixel value is multiplied by a relative radiant flux factor.

12. The non-transitory computer-readable medium of claim 9, wherein said adjusted image plane is a virtual image plane virtually positioned relative to the digital display at a designated distance from said user pupil location, and wherein said adjusted image ray trace comprises a virtual image vector between said given pixel and said given LFSE to intersect said virtual image plane.

13. The non-transitory computer-readable medium of claim 9, wherein said adjusted image plane is designated as a user retinal plane, and wherein said adjusted image ray trace is projected to intersect with said user retinal plane by redirecting said adjusted image ray trace given said pupil location in accordance with an input user eye focus aberration parameter.

14. The non-transitory computer-readable medium of claim 9, wherein said instructions are further executable to confirm that said adjusted image ray trace intersects with an input pupil area associated with said input user pupil location.

15. The non-transitory computer-readable medium of claim 9, wherein said user pupil location is dynamically tracked via a pupil or eye tracker.

16. The non-transitory computer-readable medium of claim 9, wherein the user perception is adjusted so to at least partially address the user's reduced visual acuity.

17. A digital display device operable to automatically adjust user perception of an input image to be rendered thereon, the device comprising:
an array of pixels;
an array of light field shaping elements (LFSE) to shape a light field emanating from at least some of said pixels; and
a hardware processor operable on pixel data for the input image to output adjusted image pixel data to adjust user perception of the input image as rendered by:
computing an adjusted image on an adjusted image plane corresponding to a set of display pixel values, said adjusted image being defined as a set of adjusted image pixel values corresponding to a set of image pixels or portions, and wherein:
for a trial set of display pixel values derived from said input image:
for at least some of said pixels, digitally:
projecting an adjusted image ray trace between said given pixel and a given LFSE to intersect said adjusted image plane at a given adjusted image location, given an estimated direction of a light field emanated by said given pixel given said given LFSE;
calculating a beam box region on said adjusted image plane centered on said adjusted image location characterizing the area illuminated by said given pixel;
identifying one or more image pixels overlapping with said beam box region, and;
for each of said overlapping image pixels:
adding to said image pixel value a pixel value of said display pixel;
calculating a cost function value between said adjusted image and said trial input image, said cost function value quantitatively characterizing the difference between said set of image pixel values and said input image;
deriving a new set of display pixel values reducing said cost function value;
repeating said computing an adjusted image, said calculating a cost function value and said deriving a new set of display pixel values, each time using said new set of display pixel values, until said difference parameter has been minimized; and
rendering for each pixel in said set of pixels the corresponding pixel value from said set of display pixel values corresponding to said minimized difference parameter, thereby rendering a perceptively adjusted version of the input image.

18. The device of claim 17, wherein said pixel value is multiplied by a ratio of overlap between said overlapping image pixel and said beam box before being added to said image pixel value.

19. The device of claim 17, wherein said pixel value is multiplied by a relative radiant flux factor.

20. The device of claim 17, wherein said adjusted image plane is a virtual image plane virtually positioned relative to the digital display at a designated distance from said user pupil location, wherein said adjusted image ray trace comprises a virtual image vector between said given pixel and said given LFSE to intersect said virtual image plane, and wherein said designated distance comprises a minimum viewing distance designated such that said perceptively adjusted version of the input image is adjusted to accommodate a user's reduced visual acuity.

21. The device of claim 17, wherein the device is operable to adjust user perception of the input image for viewing by a viewer having reduced visual acuity such that said perceptively adjusted version of the input image at least partially compensates for the viewer's reduced visual acuity, wherein the device further comprises a user interface for dynamically adjusting said minimum viewing distance.

22. The device of claim 17, wherein said adjusted image plane is designated as a user retinal plane, and wherein said adjusted image ray trace is projected to intersect with said user retinal plane by redirecting said adjusted image ray trace given said pupil location in accordance with an input user eye focus aberration parameter.

23. The device of claim 22, further comprising a user interface for dynamically adjusting said input user eye focus aberration parameter.

24. The device of claim 17, further comprising a pupil or eye tracker or pupil or eye tracking interface operable to dynamically track and automatically accommodate for changes in said user pupil location.

* * * * *